(12) United States Patent
Aebischer et al.

(10) Patent No.: US 6,800,281 B2
(45) Date of Patent: Oct. 5, 2004

(54) LENTIVIRAL-MEDIATED GROWTH FACTOR GENE THERAPY FOR NEURODEGENERATIVE DISEASES

(75) Inventors: Patrick Aebischer, Lausanne (CH); Susan Mary Kingsman, The Oxford Science Park (GB); Stuart Naylor, The Oxford Science Park (GB); Nicholas Mazarakis, The Oxford Science Park (GB)

(73) Assignee: Oxford Biomedica (UK) Limited, Oxford (GB)

( * ) Notice: Subject to any disclaimer, the term of this patent is extended or adjusted under 35 U.S.C. 154(b) by 19 days.

(21) Appl. No.: 10/008,610

(22) Filed: Nov. 8, 2001

(65) Prior Publication Data

US 2002/0187951 A1 Dec. 12, 2002

Related U.S. Application Data

(60) Provisional application No. 60/247,604, filed on Nov. 9, 2000.

(51) Int. Cl.[7] .................. A61K 48/00; C12N 15/867
(52) U.S. Cl. .................. 424/93.2; 424/93.1; 424/93.6; 435/320.1
(58) Field of Search ............... 435/320.1; 424/93.1, 424/93.2, 93.6

(56) References Cited

U.S. PATENT DOCUMENTS 6,683,058 B1    1/2004    Tuszynski

OTHER PUBLICATIONS

Kordower et al., Science, 2000, vol. 290, pp. 767–773.*
Marshall, Science, 2003, vol. 299, p. 320.*
Mountain, TIBTECH, 2000, vol. 18, pp. 119–128.*
Fox, Nature Biotechnology, 2000, vol. 18, pp. 143–144.*
Verma et al., Nature, 1997, vol. 389, pp. 239–242.*
Anderson, Nature, 1998, vol. 392, pp. 25–30.*
Kmiec, American Scientist, 1999, vol. 87, pp. 240–247.*

* cited by examiner

*Primary Examiner*—David Guzo
(74) *Attorney, Agent, or Firm*—Frommer Lawrence & Haug; Thomas J. Kowalski; Anne-Marie Yvon

(57) ABSTRACT

Disclosed and claimed are methods for treating or preventing neurodegenerative diseases, conditions or maladies or symptoms or physiology associated therewith, such as treating or preventing Parkinson's disease or symptoms or physiology associated therewith such as motor deficits or nigrostriatal degeneration; or, for inducing nigrostriatal regeneration. Advantageously, the methods involve administering a lentiviral vector that expresses GDNF, such as human GDNF, or a variant, homolog, analog or derivative thereof.

15 Claims, 9 Drawing Sheets

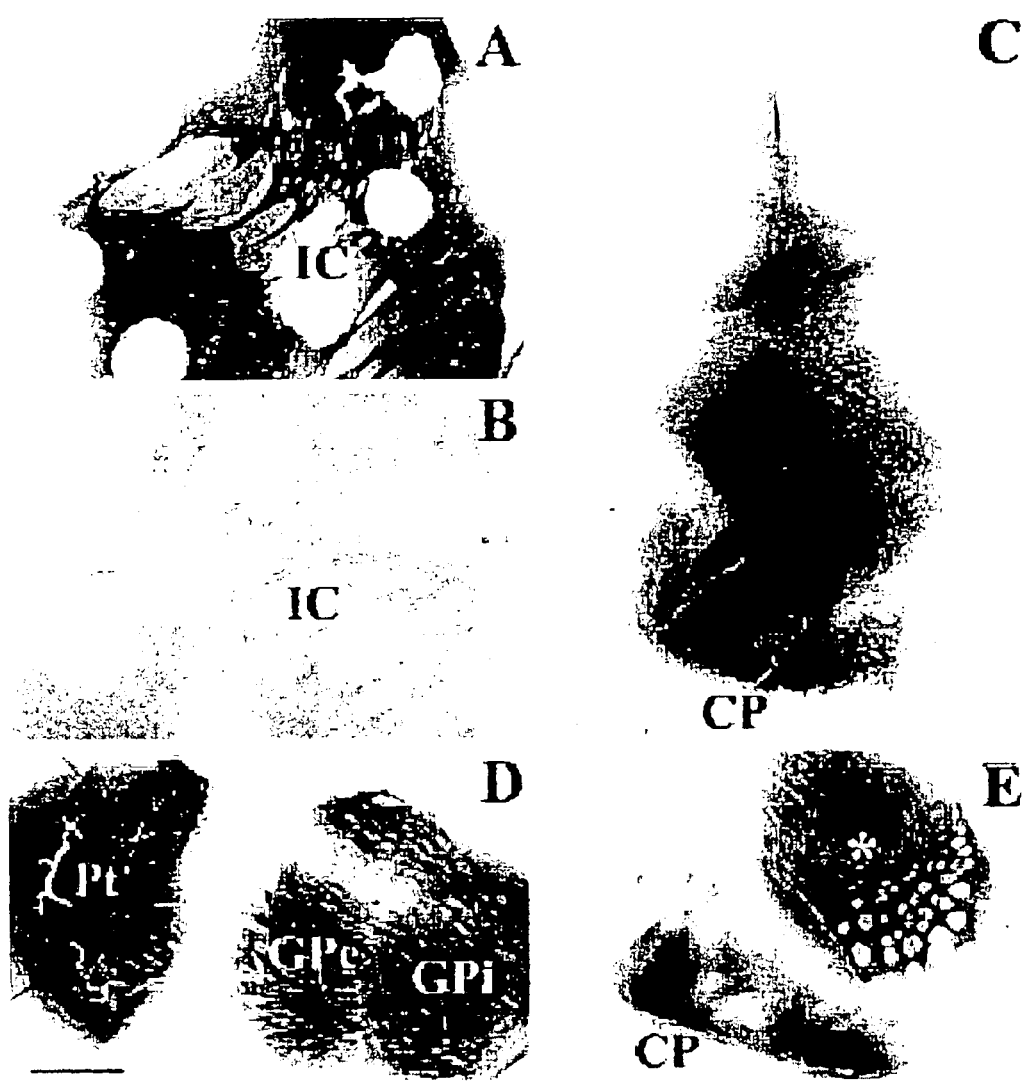
FIG. 1 (FIGS 1A-E)

FIG. 2 (FIGS 2A-D)
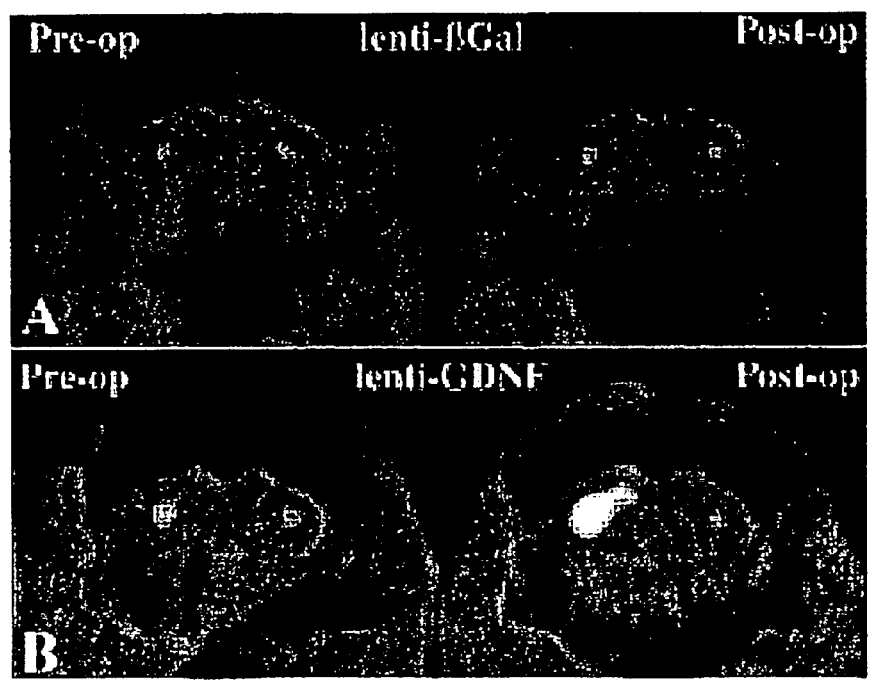
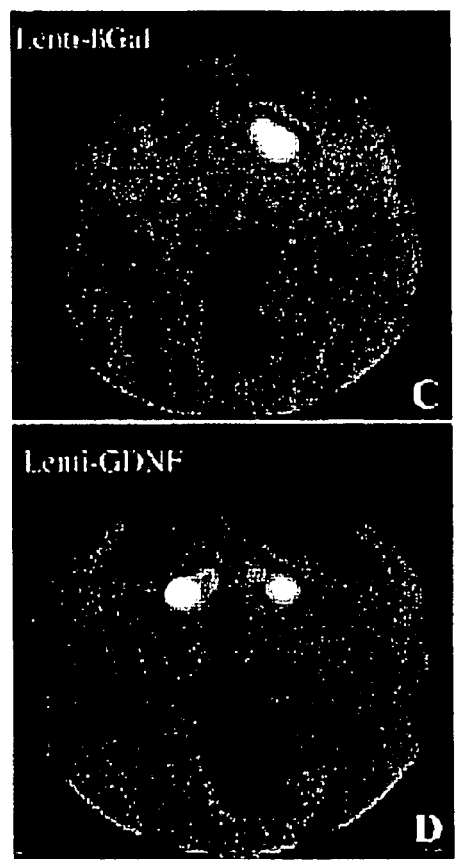

FIG. 3 (FIGS 3A-F)
A
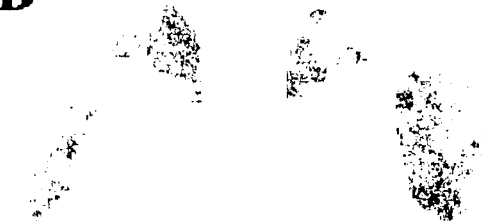
B
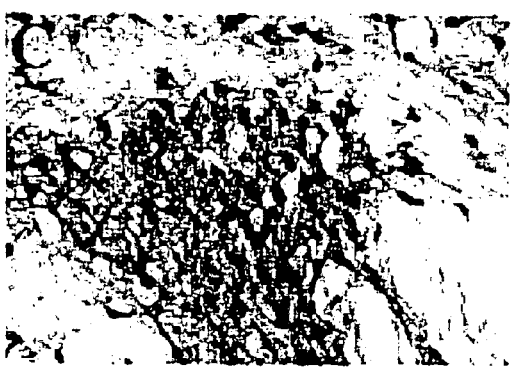
C
D
E
F FIG. 4 (FIGS 4A-F)
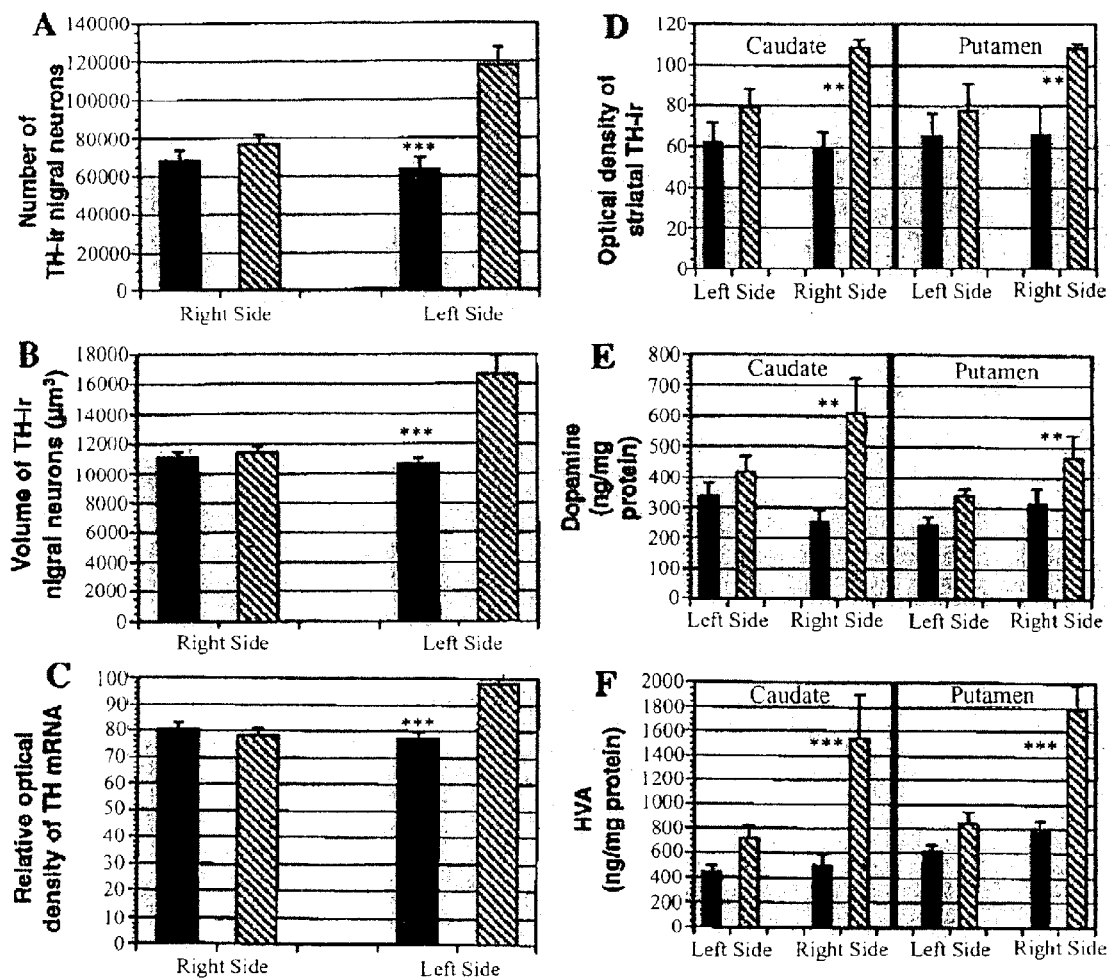

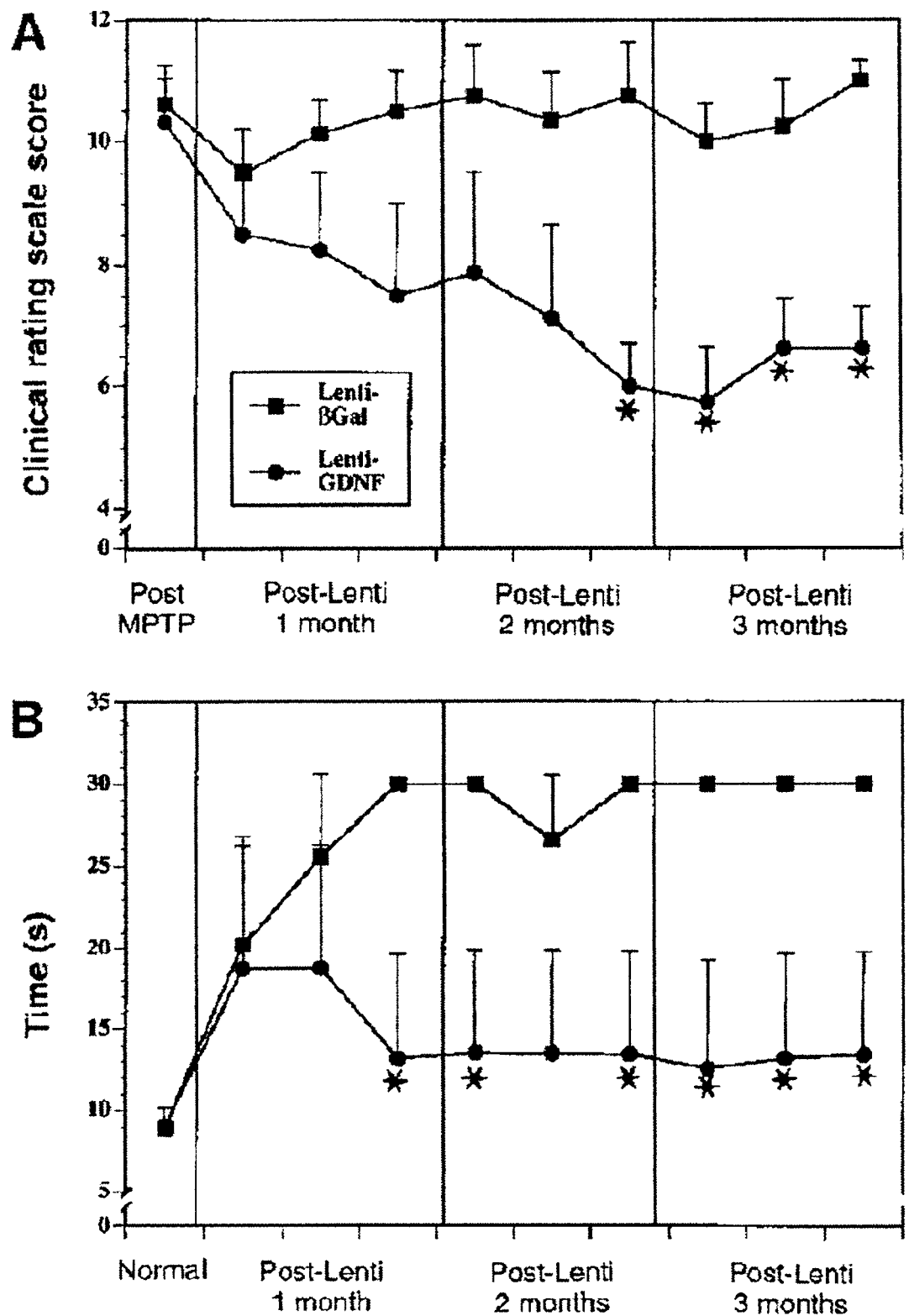
FIG. 5 (FIGS 5A-B)

FIG. 6 (FIGS 6A-H)
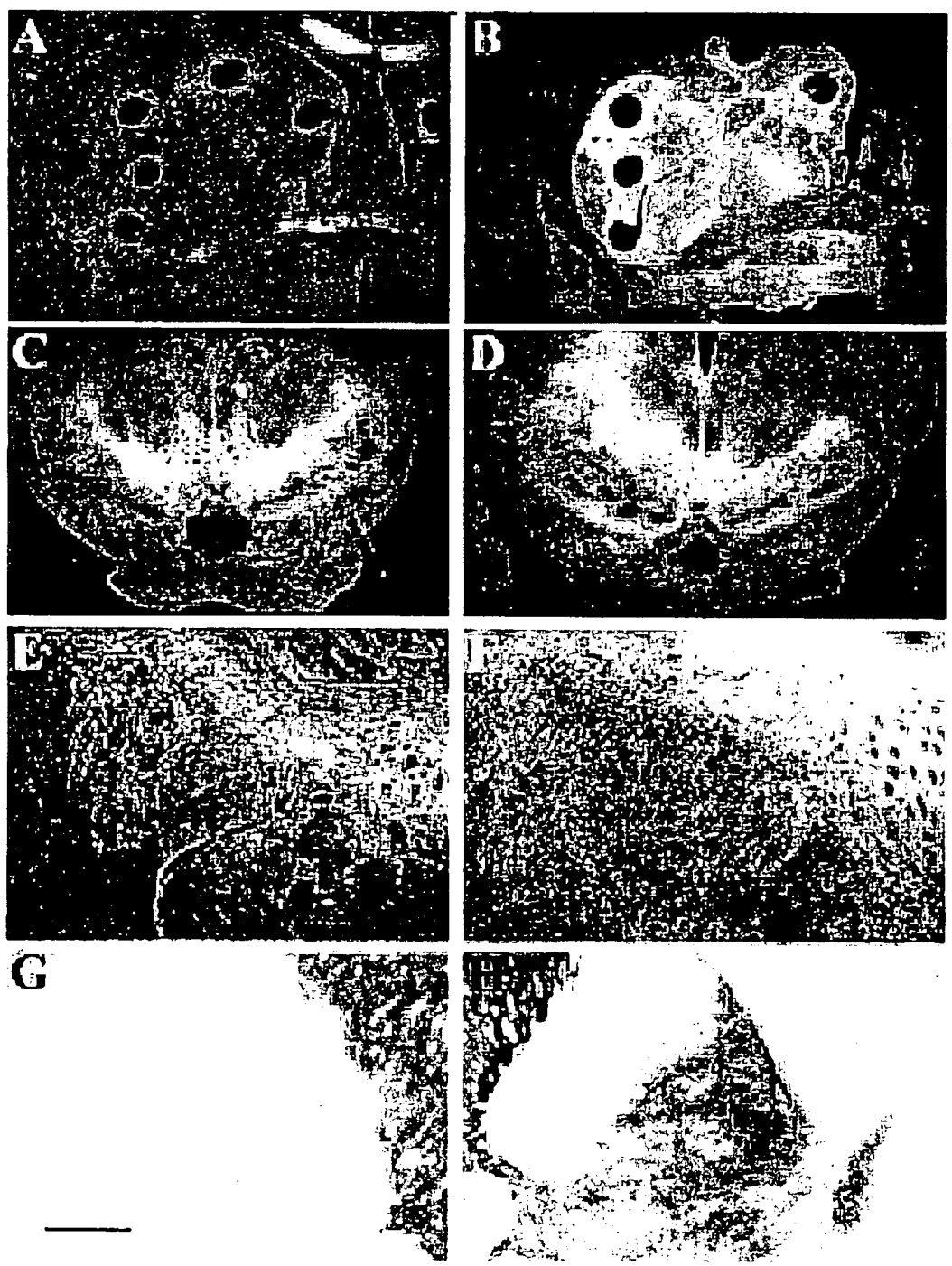

FIG. 7 (FIGS 7A-D)
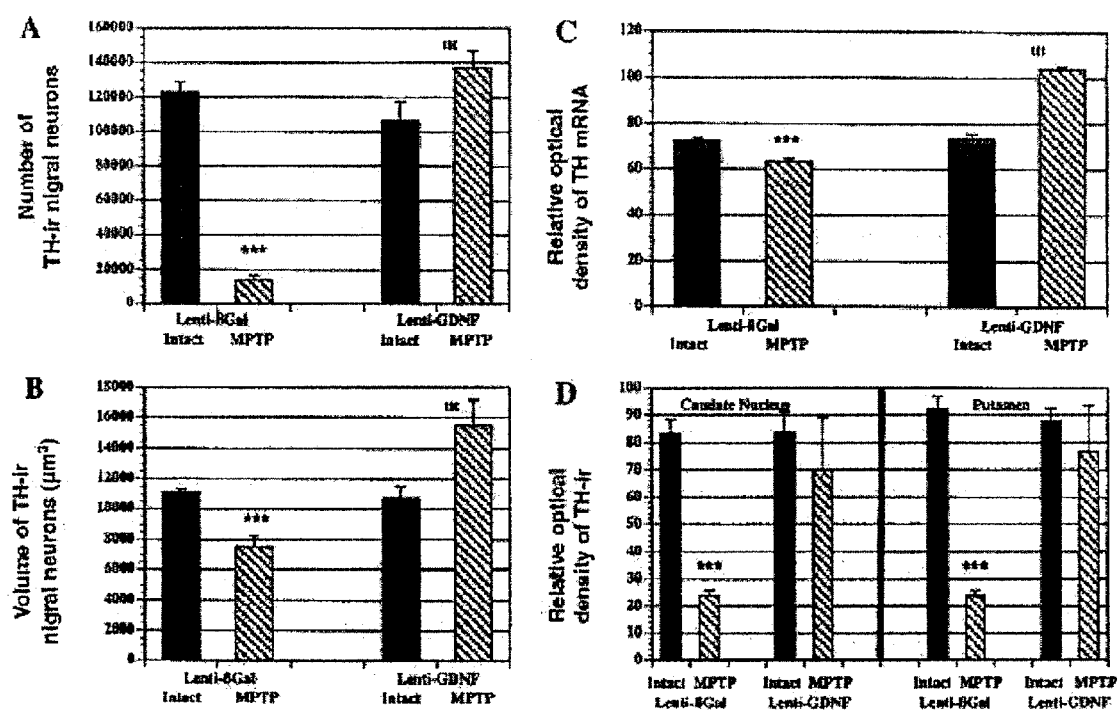

FIG. 8 (FIGS 8A-E)
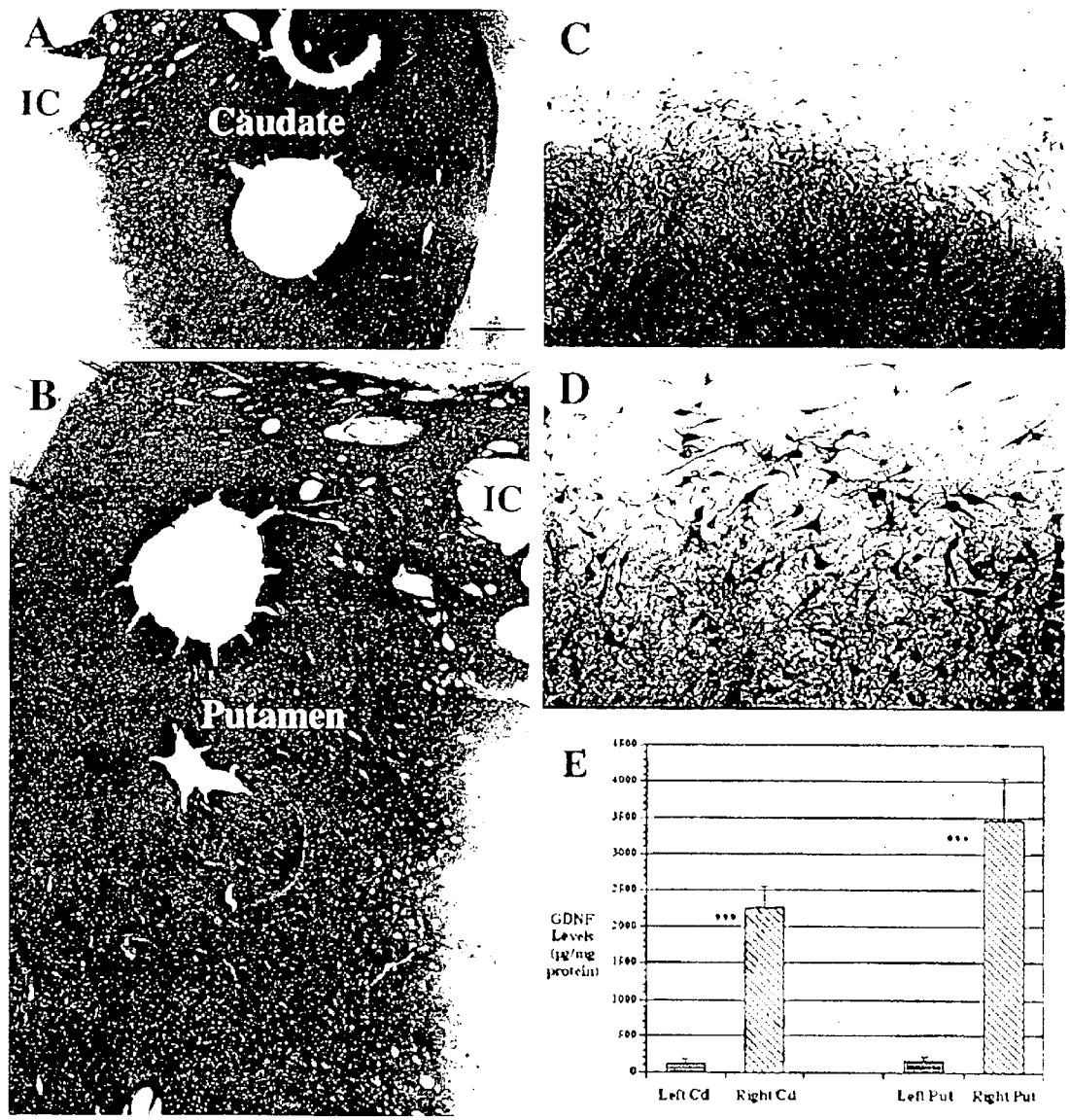

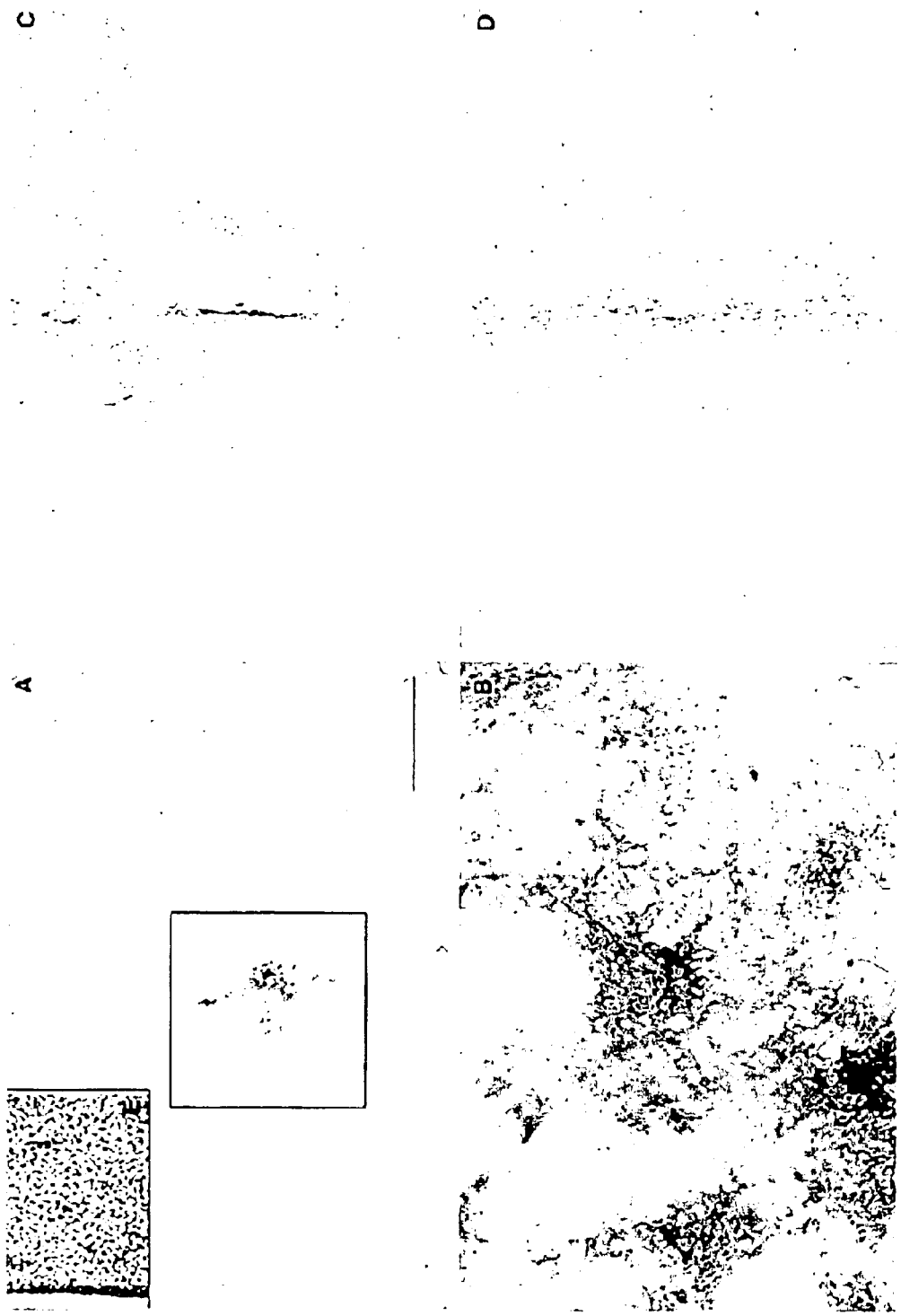
FIG. 9 (FIGS 9A-D)

LENTIVIRAL-MEDIATED GROWTH FACTOR GENE THERAPY FOR NEURODEGENERATIVE DISEASES

REFERENCE TO RELATED APPLICATIONS/INCORPORATION BY REFERENCE

This application claims priority from U.S. provisional application Ser. No. 60/247,604, filed Nov. 9, 2000.

Reference is also made to: U.S. applications Ser. Nos. 09/533,909, filed Mar. 22, 2000, 09/533,276, filed Mar. 22, 2000, 09/533,295, filed Mar. 22, 2000, 09/552,950, filed Apr. 20, 2000, and 09/656,466, filed Sep. 6, 2000; and U.S. Pat. Nos. 6,312,683, 6,312,682, 6,277,633, 6,235,522, 6,168,916, 6,132,731, 6,096,538, and 5,942,434; and UK applications Ser. Nos 0024550.6, filed Jun. 10, 2000, 9725085.6, filed Nov. 28, 1997, 9826775.0, filed Dec. 4, 1998, 9904905.8, filed Mar. 3, 1999, 9720216.2, filed Sep. 23, 1997, 9923558.2, filed Oct. 5, 1999, 0003527.9, filed Feb. 15, 2000, 0005071.6, filed Mar. 2, 2000, 0009762.6, filed Apr. 19, 2000, 0009760.0, filed Apr. 19, 2000, 0026943.1, filed Nov. 3, 2000, 0122238.9; and PCT patent applications or publications PCT/GB01/04433, filed May 10, 2001 (Vector System), PCT/GB99/04068, filed Dec. 6, 1999 and published Jun. 15, 2000, PCT/GB00/00766, filed Mar. 2, 2000 and published Sep. 8, 2000, PCT/GB98/02885, filed Sep. 23, 1998 and published Apr. 1, 1999 as WO 99/15684, PCT/GB00/04317, filed Nov. 13, 2000 and published May 25, 2001 as WO 01/25466, PCT/GB01/01784, filed Apr. 19, 2001 and published October 2001, WO 99/61639 (Retroviral Delivery System), WO 00/52188 (Packaging Cells For Retroviral Vectors), WO 00/71737 (Improved Retroviral Production), WO 00/71693 (Method For Selecting Improved Vectors), WO 00/75370 (Producer Cell For The Production of Retroviral Vectors), WO 00/56910 (Retroviral Vectors Comprising Functional and Non-Functional Splice Donor and Splice Acceptor Sites), WO 00/55341 (Anti-Viral Vectors), WO 00/31280 (Vector), WO 00/17371 (Polynucleotide Constructs And Uses Thereof), WO 99/41397 (Anti-Viral Vectors), WO 99/32646 (Equine Infectious Anemia Virus (EIAV) Based), WO 99/15683 (Retroviral Vectors Comprising A Functional Splice Donor and A Functional Splice Acceptor Site), WO 98/55640 (Retroviral Vector Particles Produced In a Baculovirus Expression System), WO 98/55607 (Vector), WO 98/18934 (Therapeutic Gene), WO 98/17817 (Retroviral Vectors), WO 98/17816 (Lentiviral Vectors), WO 98/17815 (Retroviral Vectors), WO 97/32026 (Adapter Molecules For Targeting Viral Particles Tod Cells), WO 97/27310 (Retroviral Vector And Its Use In Gene Therapy), WO 97/22709 (Host Adaption of Retroviral Vectors), and WO 96/37623 (Retroviral Vectors), and Zurn, Widmer, and Aebischer, "Sustained delivery of GDNF: towards a treatment for Parkinson's disease," Brain Res Brain Res Rev 36(2–3):222–9 (October 2001), and Kordower et al., "Neurodegeneration Prevented by Lentiviral Vector Delivery of GDNF in Primate Models of Parkinson's Disease," Science 290:767–773 (Oct. 27, 2000).

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity. Thus, for instance, it is explicitly stated that the foregoing Kordower et al. and Zurn et al. articles are not "by another" or and Kordower et al. and Zurn et al. are not "others" as to the present inventive entity and vice versa.

Research with respect to disclosure herein may have been supported by a grant from the Department of Defense, The Charles Shapiro Foundation, NS40578, and by the Swiss National Science Foundation and the Swiss National Program in Neurological Diseases. There is no admission that any of the potential supporters or grantors have any rights.

FIELD OF THE INVENTION

The present invention relates to a vector system, such as a lentiviral vector system for the treatment of neurodegenerative disease in a mammal, e.g., Parkinson's disease.

Further, the present invention relates to a method for treating a neurodegenerative disease and/or symptoms thereof and/or preventing neurodegenerative disease and/or symptoms thereof, in a mammal, comprising, administering a lentiviral vector to a target cell in the brain or nervous system of the mammal, said lentiviral vector comprising a nucleic acid sequence comprising a sequence encoding a growth factor, advantageously in operable linkage with or operably linked to a promoter sequence, wherein said growth factor is expressed in the target cell, thereby treating said neurodegenerative disease. Advantageously the lentiviral vector is primate or non-primate lentiviral vector such as an EIAV vector or an HIV vector or an SIV vector or an FIV vector. Also advantageously, the growth factor is a GDNF, such as a human GDNF. The GDNF can be modified and the nucleic acid molecule encoding the GDNF can likewise be modified; for instance due to the degeneracy of codon usage, the GDNF coding sequence can be modified, and truncated forms of GDNF can be used, such as those which may be found in the literature. Likewise, analogs, homologs, derivatives, and variants of the GDNF coding sequence can be used and ergo of analogs, homologs, derivatives and variants of GDNF can be expressed; advantageously such expressed analogs, homologs, derivatives and variants of GDNF have activity analogous to that of full length human GDNF, e.g., as employed in the exemplified embodiment herein, and the analogs, homologs, derivatives and variants of the GDNF coding sequence encode such active GDNF analogs, homologs, derivatives, and variants. The mammal is advantageously a primate, such as a human. The administration can be by stereotaxic injection. The administration can be intracranially, e.g., intracranially to stiatum or to substantia nigra. The administration can also be by retrograde transport. The neurodegenerative disease can be Parkinson's disease. The treating of Parkinson's disease can be by prevention of nigrostriatal degeneration and/or induction of nigrostriatal regeneration and/or reversal of motor deficits. And, the growth factor expression can be for up to 8 months.

Even further still, the lentiviral vector can include additional nucleic sequences, such as nucleic acid sequences encoding one or more other members of the GDNF-family of neurotrophic factors, e.g., neurturin, persphin, neublastin, artemin; and/or the lentiviral vector can contain one or more other nucleotide sequences encoding expression products suitable for treating a neurdegenerative disorder, such as Tyrosine Hydroxylase, GTP-cyclohydrolase I, Aromatic Amino Acid Dopa Decarboxylase and Vesicular Monoamine Transporter 2 (VMAT2), preferably nucleic acid sequences encoding Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2. These other nucleotide sequences may also encode proteins such as growth factors, e.g., NGF (nerve growth factor) and BDNF (brain-derived neurotrophic factor), and antibodies.

Additionally or alternatively, the lentiviral vector encoding the growth factor, e.g., GDNF, can be administered with one or more additional vectors containing one or more additional nucleic acid sequences, such as nucleic acid sequences encoding one or more other members of the GDNF-family of neurotrophic factors, e.g., neurturin, persphin, neublastin, artemin, and/or other nucleotide sequences encoding expression products suitable for treating a neurdegenerative disorder, such as Tyrosine Hydroxylase, GTP-cyclohydrolase I, Aromatic Amino Acid Dopa Decarboxylase and Vesicular Monoamine Transporter 2 (VMAT2), preferably encoding Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2. These other nucleotide sequences may also encode proteins such as growth factors and antibodies. The one or more additional vector can be any suitable vector such as an adenovirus or lentiviral vector; and, it is presently preferred and considered advantageous that the additional vector be a lentiviral vector, as AAV and adenovirus systems, as herein further discussed, do not obtain the enhanced effects observed with the lentiviral-growth factor, e.g., lentiviral-GDNF of the present invention. "Administration with" the lentiviral vector encoding the growth factor, e.g., GDNF, can be through simultaneous administration, e.g., the vectors are admixed in a single formulation that is administered, or via sequential or concomitant administration of the vectors or formulations containing the vectors.

When a vector genome such as a lentiviral or retroviral vector genome comprises two or more nucleic acid sequences (also known as nucleotide sequences of interest or NOIs), it is advantageous that they are operably linked by one or more Internal Ribosome Entry Site(s), e.g., a genome, advantageously a lentiviral genome, comprising three or more NOIs operably linked by two or more Internal Ribosome Entry Site(s) wherein preferably each NOI is useful in the treatment of a neurodegenerative disorder and at least one of the NOIs is a growth factor such as GDNF.

The invention also relates to vector systems, advantageously lentiviral vector systems, used in the methods of the invention, such as a lentiviral vector system which is capable of delivering an RNA genome to a recipient cell, wherein the genome is longer than the wild type genome of the lentivirus, e.g., an EIAV vector system.

According to further aspects of the invention relates to:
a method for producing a lentiviral particle which comprises introducing such a viral genome into a producer cell;

a viral particle produced by such a system or method;

a pharmaceutical composition comprising such a genome, system or particle;

the use of such a genome, system or particle in the manufacture of a pharmaceutical composition to treat and/or prevent a disease;

a cell which has been transduced with such a system;

a method of treating and/or preventing a disease by using such a genome, system, viral particle or cell;

Thus, the invention relates to pharmaceutical compositions comprising the lentiviral vector or the lentiviral vector and other vector(s) employed in the methods of the invention, as well as kits for preparing such compositions (e.g., the lentiviral vector or the lentiviral vector and the other vector(s) in one or more containers and pharmaceutically acceptable excipient, carrier, diluent, adjuvant, and the like in one or more additional containers, wherein said containers can be provided in one or more packages, for instance, packaged together or separately, and optionally including instructions for admixture and/or administration).

The invention can also relate to a bicistronic cassette comprising a nucleotide sequence capable of encoding the growth factor, e.g., GDNF, and an additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein, operably linked by one or more IRES(s). The invention likewise can also relate to tricistronic cassettes comprising a nucleotide sequence capable of encoding the growth factor, e.g., GDNF, and a first additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein and a second additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein, operably linked by two or more IRES(s). Further cassettes are envisioned by the invention.

In addition, it is noted that while herein text may mention employing nucleotide sequences capable of encoding one or more other GDNF-family of neurotrophic factors, e.g., as additional sequences in lentiviral vectors such as lentiviral-growth factor, e.g., lentiviral-GDNF vectors, or in additional vectors administered with lentiviral vectors such as lentiviral-growth factor, e.g., lentiviral-GDNF vectors, such embodiments are not presently preferred because, as discussed below, work involving lentiviral-GDNF-family-gene-neublastin/artemin reported in the literature has not been reproducible.

Further aspects of the invention are described herein.

BACKGROUND

Parkinson's disease (PD) is a neurodegenerative disorder characterized by the loss of the nigrostriatal pathway; a progressive disorder resulting from degeneration of dopaminergic neurons within the substantia nigra. Although the cause of Parkinson's disease is not known, it is associated with the progressive death of dopaminergic (tyrosine hydroxylase (TH) positive) mesencephalic neurons, inducing motor impairment. The characteristic symptoms of Parkinson's disease appear when up to 70% of TH-positive nigrostriatal neurons have degenerated. Surgical therapies aimed at replacing lost dopaminergic neurons or disrupting aberrant basal ganglia circuitry have recently been tested (C. Honey et al. 1999). However, these clinical trials have focused on patients with advanced disease, and the primary goal of forestalling disease progression in newly diagnosed patients has yet to be realized.

Thus, there is currently no satisfactory cure for Parkinson's disease or treatments for preventing or treating Parkinson's disease or its symptoms.

Symptomatic treatment of the disease-associated motor impairments involves oral administration of dihydroxyphenylalanine (L-DOPA). L-DOPA is transported across the blood-brain barrier and converted to dopamine, partly by residual dopaminergic neurons, leading to a substantial improvement of motor function. However, after a few years, the degeneration of dopaminergic neurons progresses, the effects of L-DOPA are reduced and side-effects reappear.

Better therapy for preventing, treating and/or curing Parkinson's disease and/or symptoms thereof is therefore necessary and desirable.

An alternative strategy for therapy is neural grafting, which is based on the idea that dopamine supplied from cells implanted into the striatum can substitute for lost nigrostriatal cells. Clinical trials have shown that mesencephalic TH positive neurons obtained from human embryo cadavers (aborted foetuses) can survive and function in the brains of patients with Parkinson's disease. However, functional recovery has only been partial, and the efficacy and reproducibility of the procedure is limited. Also, there are ethical, practical and safety issues associated with using tissue derived from aborted human foetuses. Moreover, the large amounts of tissue required to produce a therapeutic effect is likely to prove to be prohibitive. Some attempts have been made to use TH positive neurons from other species (in order to circumvent some of the ethical and practical problems). However, xenotransplantation requires immunosuppressive treatment and is also controversial due to, for example, the possible risk of cross-species transfer of infectious agents. Another disadvantage is that, in current grafting protocols, no more than 5–20% of the expected numbers of grafted TH positive neurons survive. In order to develop a practicable and effective transplantation protocol, an alternative source of TH positive neurons is required.

A further alternative strategy for therapy is gene therapy: replace dopamine in the affected striatum by introducing the enzymes responsible for L-DOPA or dopamine synthesis (for example, tyrosine hydroxylase); or introduce potential neuroprotective molecules that may either prevent the TH-positive neurons from dying or stimulate regeneration and functional recovery in the damaged nigrostriatal system (Dunnet S. B. and Björklund A. (1999) Nature 399 A32–A39).

In vivo, dopamine is synthesised from tyrosine by two enzymes, tyrosine hydroxylase (TH) and aromatic amino acid DOPA-decarboxylase (AADC). Parkinson's disease has been shown to be responsive to treatments that facilitate dopaminergic transmission in caudate-putamen. In experimental animals, genetically modified cells that express tyrosine hydroxylase, and thereby synthesise L-DOPA, induce behavioural recovery in rodent models of PD (Wolff etal. (1989) PNAS (USA) 86:9011–14; Freed et al (1990) Arch. Neurol. 47:505–12; Jiao et al. (1993) Nature 262:4505). However, the functional activity of tyrosine hydroxylase depends on the availability of its cofactor tetrahydrobiopterin ($BH_4$). The level of cofactor may be insufficient in the denervated striatum, and so it is thought that GTP cyclohydrolase I, the enzyme that catalyses the rate limiting step on the pathway of $BH_4$-synthesis, may also need to be transduced to obtain sufficient levels of L-DOPA production in vivo (Bencsics et al (1996) J. Neurosci 16:4449–4456; Leff et al (1998) Exp. Neurol. 151:249–264).

Kaplitt U.S. Pat. No. 6,180,613, and Choi-Lundberg et al. 1997 involve as AAV and Adenoviral vectors, in contrast to the lentiviral vectorsin the present invention, which surprisingly obtain the enhanced effects reported herein such that the work of Kaplitt et al. and Choi-Lundberg et al. fail to teach or suggest the present invention.

C. Rosenblad et al. 2000 reports allegedly using lentiviral vectors to deliver the neublastin/artemin gene. This is a different gene altogether than the gene encoding growth factor GDNF employed in the present invention; and, the neublastin/artemin gene is known not to work and the experiment reported in C. Rosenblad et al. 2000 is not reproducible as the present inventor indeed has tried to do so, and has been unable to reproduce the work of C. Rosenblad et al.

Therefore, although in vivo and ex vivo gene therapy strategies may have been proposed (Dunnet and Bjorklund (1999) as above; Raymon et al (1997) Exp. Neurol. 144:82–91; Kang (1998) Mov. Dis. 13: 59–72) significant progress in this technology has been hampered by many factors, such as the limited efficiency of gene transfer and expression in the target cells, non-reproducible results, and the like. One particular problem in this regard is that the target cells are usually non-dividing cells (i.e. neurones) which are notoriously recalcitrant to transduction. Accordingly, previous therapy strategies fail to teach or suggest the present invention which is herein demonstrated with respect to primates—mammals close to humans and most indicative of the surprising superiority achieved by the present invention.

WO 98/18934 relates to a polynucleotide sequence for use in gene therapy, which polynucleotide sequence comprises two or more genes operably linked to a promoter, and encodes a fusion protein product of the therapeutic genes. This provides a way of expressing two therapeutic genes from a single "chimeric gene". The polynucleotide sequence is capable of encoding a fusion protein comprising tyrosine hydroxylase and DOPA decarboxylase in either TH-DD or DD-TH order, linked by a flexible linker. WO/18924, involves gene transfer systems such as retroviral vectors; and there are other documents that may involve retroviral vectors (See, e.g., Naldini et al., 1996 Science 272, 263; PCT/GB96/01230; Bowtell et al., 1988 J.Virol. 62, 2464; Correll et al., 1994 Blood 84, 1812; Emerman and Temin 1984 Cell 39, 459; Ghattas et al., 1991 Mol.Cell.Biol. 11, 5848; Hantzopoulos et al., 1989 PNAS 86, 3519; Hatzoglou et al., 1991 J.Biol.Chem 266, 8416; Hatzoglou et al., 1988 J.Biol.Chem 263, 17798; Li et al., 1992 Hum.Gen.Ther. 3, 381; McLachlin et al., 1993 Virol. 195, 1; Overell et al., 1988 Mol.Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197; WO99/15683; Verma and Somia (1997) Nature 389:239–242; page 446, Chapter 9 of Coffin et al "Retroviruses" 1997 Cold Spring Harbour Laboratory Press).

WO 98/18934 involves expressing two proteins from a single retroviral vector as a fusion protein (encoded by a single nucleotide sequence) rather than the use of an internal ribosome entry site (IRES) to initiate translation of the second coding sequence in a poly-cistronic message, whereas an IRES, when located between open reading frames in an RNA allows translation of the downstream open reading frame by promoting entry of the ribosome at the IRES element followed by downstream initiation of translation (See WO 9310314).

However, heretofore the use of IRES elements in retroviral vector systems has not been favored because expression of the coding sequence situated downstream of the IRES has often been found to be inefficient, perhaps due to competition for ribosomes and other cellular factors; and, the efficiency of translation initiation would therefore be expected to decrease with increasing numbers of IRES elements.

In addition, another aspect of the art directing against embodiments of the present invention, such as those wherein there is expression of more than one gene, is that there are believed limits on the size of the heterologous gene which can be successfully transduced; and, if incorporation of the heterologous genes and associated regulatory elements dramatically increases the size of the viral genome, then there is a significant risk that it will no longer be able to be successfully packaged, or at least that packaging efficiency will be significantly reduced.

Accordingly, heretofore there has been a need not yet met for gene therapy approaches to treating, preventing, or curing neurodegenerative conditions such as Parkinson's disease or symptoms thereof; the superior in vivo expression and results obtained therefrom by a lentiviral-growth factor vector, e.g., a lentiviral-GDNF vector, as herein reported, are surprising and unexpected; and, the use of such a vector—either alone or in combination with other vectors or as a vector that expresses additional products—especially in treatment, prevention and the like of neurodegenerative conditions such as Parkinson's disease or symptoms thereof is surprising and unexpected.

SUMMARY OF THE INVENTION

Lentiviral delivery of a growth factor, such as glial cell line-derived neurotrophic factor (lenti-GDNF) was tested for its trophic effects upon degenerating nigrostriatal neurons in nonhuman primate models of Parkinson's disease (PD). Lentiviral-GDNF vectors were injected into the striatum and substantia nigra of nonlesioned aged rhesus monkeys or young adult rhesus monkeys treated 1 week prior with 1-methyl-4-phenyl-1,2,3,6-tetrahydropyridine (MPTP). Extensive GDNF expression with anterograde and retrograde transport was seen in all animals. In aged monkeys, lentiviral-GDNF vectors augmented dopaminergic function. In MPTP-treated monkeys, lentiviral-GDNF vectors reversed functional deficits and completely prevented nigrostriatal degeneration. Additionally, lentiviral-GDNF vectors injections to intact rhesus monkeys revealed long-term gene expression (at least 8 months). In MPTP-treated monkeys, lentiviral-GDNF vector treatment reversed motor deficits in a hand-reach task. These data indicate that GDNF delivery using a lentiviral vector system can prevent nigrostriatal degeneration and induce regeneration in PD and are thus a viable therapeutic strategy for PD patients and patients with neurodegenerative conditions.

Accordingly, the present invention provides a vector system, such as a lentiviral vector system for the treatment of neurodegenerative disease in a mammal, e.g., Parkinson's disease.

Further, the present invention provides a method for treating a neurodegenerative disease and/or symptoms thereof and/or preventing neurodegenerative disease and/or symptoms thereof, in a mammal, comprising, administering a lentiviral vector to a target cell in the brain or nervous system of the mammal, said lentiviral vector comprising a nucleic acid sequence comprising a sequence encoding a growth factor, advantageously in operable linkage with or operably linked to a promoter sequence, wherein said growth factor is expressed in the target cell, thereby treating said neurodegenerative disease.

Advantageously the lentiviral vector is an EIAV vector or an HIV vector or an SIV vector or an FIV vector.

Also advantageously, the growth factor is a GDNF, such as a human GDNF.

The invention comprehends that the human GDNF can be modified and that the nucleic acid molecule encoding the human GDNF can likewise be modified; for instance due to the degeneracy of codon usage, the human GDNF coding sequence can be modified, and modified and truncated forms of GDNF can be used, such as those which may be found in the literature or analogous to truncated or modified forms found in the literature.

Likewise, analogs, homologs, derivatives, and variants of the human GDNF coding sequence can be used and ergo of analogs, homologs, derivatives and variants of human GDNF can be expressed; advantageously such expressed analogs, homologs, derivatives and variants of human GDNF have activity analogous to that of full length human GDNF, e.g., as employed in the exemplified embodiment herein, and the analogs, homologs, derivatives and variants of the human GDNF coding sequence encode such active GDNF analogs, homologs, derivatives, and variants.

As discussed herein analogs, homologs, derivatives, and variants of human GDNF have homology with GDNF, e.g., at least 75%, preferably at least 85%, more preferably at least 90%, advantageously at least 95%, and more advantageously at least 98% homology with the human GDNF sequence; and, the analog, homolog, derivative and variant advantageously has GDNF activity. One can determine, without undue experimentation, where such variations in human GDNF can be made by comparing, for instance, the GDNFs of various species and noting the differences among them (such differences provide the nature and location of changes to human GDNF that still result in active GDNF), as well as by considering truncated or modified versions of GDNFs that exist in the literature.

Analogs, homologs, variants and derivatives of the sequence encoding human GDNF have at least 75%, preferably at least 85%, more preferably at least 90%, advantageously at least 95%, and more advantageously at least 98% homology; with the human GDNF coding sequence and, the polypeptide advantageously has GDNF activity. One can determine, without undue experimentation, where such variations in the human GDNF coding sequence can be made by considering the degeneracy of codon usage, comparing, for instance, the GDNFs of various species and noting the differences among them (such differences provide the nature and location of changes to human GDNF that still result in active GDNF and the nucleic acid molecule coding sequence can be likewise varied), comparing the nucleic acid molecule coding sequences for GDNFs of various species (as that shows where differences are in coding sequences that still result in a functional GDNF), as well as by considering truncated or modified versions of GDNFs that exist in the literature and nucleic acid molecules encoding such modified or truncated versions of GDNFs.

For instance, an analog, homolog, derivative, or analog of the coding sequence human GDNF can be a nucleic acid molecule that hybridizes specifically to a the coding sequence for human GDNF As mentioned, an analog, homolog, derivative or variant can be a codon equivalent nucleic acid molecule to the coding sequence for human GDNF. For instance, in generic terms if the invention comprehends "X" protein (e.g., human GDNF) having amino acid sequence "A" and nucleic acid molecule "N" encoding protein X, the invention comprehends nucleic acid molecules that also encode protein X via one or more different codons than in nucleic acid molecule N.

Similarly, the invention envisions polypeptides wherein amino acids are substituted from those of disclosed sequences on the basis of charge and/or structural similarities. That is, in determining suitable analogs, homologs, derivatives or variants of human GDNF, the skilled artisan, without undue experimentation, can consider replacing amino acids in therein with amino acids of similar charge and/or structure so as to obtain a variant, homolog, derivative or variant; and, from making such changes, the skilled artisan can derive a suitable nucleic acid molecule coding sequence for the variant, homolog, derivative, or variant of GDNF, without any undue experimentatioin Thus, the skilled artisan can consider charge and/or structure of human GDNF sequences or portions thereof, in constructing homolgs, variants, analogs and derivatives and nucleic acid molecules coding therefor, without undue experimentation.

In addition, as to nucleic acid molecules encoding human GDNF, the invention comprehends nucleic acid molecules that hybridize under stringent conditions thereto as well as under high stringency conditions thereto and, hybridizing or hybridization under stringent conditions and high stringency conditions can be synonymous with stringent hybridization conditions, terms which are well known in the art; see, for example, Sambrook, "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985; both incorporated herein by reference. Thus, specific hybridization of nucleic acid molecules to the nucleic acid molecule encoding human GDNF preferably occurs at stringent hybridization conditions.

One skilled in the art can obtain variants, homologs, analogs or derivatives of human GDNF by PCR, for instance, by PCR amplification of a sample containing a GDNF using a probe or primer or probes or primers that (each) can be any stretch of at least 8, preferably at least 10, more preferably at least 12, 13, 14, or 15, such as at least 20, e.g., at least 23 or 25, for instance at least 27 or 30 contiguous nucleotides in a human GDNF nucleic acid molecule (sequence) which are unique thereto. As to PCR or hybridization primers or probes and optimal lengths therefor, reference is also made to Kajimura et al., GATA 7(4):71–79 (1990).

"Homology" is a well known term. Sequence homology or identity or similarity such as nucleotide sequence homology can be determined using the "Align" program of Myers and Miller, ("Optimal Alignments in Linear Space", CABIOS 4, 11–17, 1988, incorporated herein by reference) and available at NCBI, as well as the same or other programs available via the Internet at sites thereon such as the NCBI site. Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}$=8; $N_{dif}$=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

Additionally or alternatively, sequence identity or similarity or homology such as amino acid sequence similarity or identity or homology can be determined using the BlastP program (Altschul et al., Nucl. Acids Res. 25, 3389–3402, incorporated herein by reference) and available at NCBI, as well as the same or other programs available via the Internet at sites thereon such as the NCBI site. The following references (each incorporated herein by reference) provide algorithms for comparing the relative identity or homology or similarity of sequences such as amino acid residues of two proteins, and additionally or alternatively with respect to the foregoing, the teachings in these references can be used for determining percent homology or identity: Needleman S B and Wunsch CD, "A general method applicable to the search for similarities in the amino acid sequences of two proteins," *J. Mol Biol* 48:444–453 (1970); Smith T F and Waterman M S, "Comparison of Bio-sequences," *Advances in Applied Mathematics* 2:482–489 (1981); Smith T F, Waterman M S and Sadler J R, "Statistical characterization of nucleic acid sequence functional domains," *Nucleic Acids Res.,* 11:2205–2220 (1983); Feng D F and Dolittle R F, "Progressive sequence alignment as a prerequisite to correct phylogenetic trees," *J. of Molec. Evol.,* 25:351–360 (1987); Higgins D G and Sharp P M, "Fast and sensitive multiple sequence alignment on a microcomputer," *CABIOS,* 5: 151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.,* 22:4673–480 (1994); and, Devereux J, Haeberlie P and Smithies O, "A comprehensive set of sequence analysis program for the VAX," *Nucl. Acids Res.,* 12: 387–395 (1984). And, without undue experimentation, the skilled artisan can consult with many other programs or references for determining percent homology.

Thus, without undue experimentation from this disclosure and the knowledge in the art, the skilled artisan can construct a lentiviral vector containing a coding sequence for a variant, homolog, analog or derivative of human GDNF that encodes and expresses a polypeptide that is functional as a human GDNF, e.g., a variant, homolog, analog, or derivative of human GDNF.

The mammal is advantageously a primate, such as a human.

The administration can be by stereotaxic injection.

The administration can be intracranially, e.g., intracranially to stiatum or to substantia nigra.

The administration can also be by retrograde transport.

The present invention provides the use of a vector system to transduce a target site, wherein the vector system travels to the site by retrograde transport. With respect to retrograde transport, reference is made to UK applications 0122238.9 and 0026943.1 and the corresponding PCT application which claims priority to these UK applications.

The cell body is where a neuron synthesises new cell products. Two types of transport systems carry materials from the cell body to the axon terminals and back. The slower system, which moves materials 1–5 mm per day is called slow axonal transport. It conveys axoplasm in one direction only (from the cell body toward the axon terminals (anterograde transport)). There is also "Fast transport" which is responsible for the movement of membranous organelles at 50–200 mm per day away from the cell body (anterograde) or back to the cell body (retrograde) (Hirokawa (1997) Curr Opin Neurobiol 7(5):605–614).

Vector systems comprising rabies G protein are capable of retrograde transport (i.e. travelling towards the cell body). The precise mechanism of retrograde transport is unknown, however. It is thought to involve transport of the whole viral particle, possibly in association with an internalised receptor. The fact that vector systems comprising rabies G can be specifically be transported in this manner (as demonstrated herein) suggests that the env protein may be involved.

HSV, adenovirus and hybrid HSV/adeno-associated virus vectors have all been shown to be transported in a retrograde manner in the brain (Horellou and Mallet (1997) Mol Neurobiol 15(2) 241–256; Ridoux et al (1994) Brain Res 648:171–175; Constantini et al (1999) Human Gene Therapy 10:2481–2494). Injection of Adenoviral vector system expressing glial cell line derived neurotrophic factor (GDNF) into rat striatum allows expression in both dopaminergic axon terminals and cell bodies via retrograde transport (Horellou and Mallet (1997) as above; Bilang-Bleuel et al (1997) Proc. Natl. Acd. Sci. USA 94:8818–8823).

Retrograde transport can be detected by a number of mechanisms known in the art. In the present examples, a vector system expressing a heterologous gene is injected into the striatum, and expression of the gene is detected in the substantia nigra. It is clear that retrograde transport along the neurons which extend from the substantia nigra to the basal ganglia is responsible for this phenomenon. It is also known to monitor labelled proteins or viruses and directly monitor their retrograde movement using real time confocal microscopy (Hirokawa (1997) as above).

By retrograde transport, it is possible to get expression in both the axon terminals and the cell bodies of transduced neurons. These two parts of the cell may be located in distinct areas of the nervous system. Thus, a single administration (for example, injection) of the vector system of the present invention may transduce many distal sites.

The present invention thus also provides the use of a vector system where the vector system is or comprises at least part of rabies G to transduce a target site, which comprises the step of administration of the vector system to an administration site which is distant from the target site.

The target site may be any site of interest which is anatomically connected to the administration site. The target site should be capable of receiving vector from the administration site by axonal transport, for example anterograde or (more preferably) retrograde transport. For a given administration site, a number of potential target sites may exist which can be identified using retrograde tracers by methods known in the art (Ridoux et al (1994) as above).

For example, intrastriatal injection of HSV/AAV amplicon vectors causes transgene expression in the substantia nigra, cortex, several thalamic nuclei (posterior, paraventricular, parafasicular, reticular), prerubral field, deep mesencephalic nuclei, mesencephalic grey nucleus, and intrastitial nucleus of the medial as well as dorsal longitudinal fasiculus (Constantini et al (1999) as above).

A target site is considered to be "distant from the administration" if it is (or is mainly) located in a different region from the administration site. The two sites may be distinguished by their spatial location, morphology and/or function.

In the brain, the basal ganglia consist of several pairs of nuclei, the two members of each pair being located in opposite cerebral hemispheres. The largest nucleus is the corpus striatum which consists of the caudate nucleus and the lentiform nucleus. Each lentiform nucleus is, in turn, subdivided into a lateral part called the putamen and a medial part called the globus pallidus. The substantia nigra and red nuclei of the midbrain and the subthalamic nuclei of the diencephalon are functionally linked to the basal ganglia. Axons from the substantia nigra terminate in the caudate nucleus or the putamen. The subthalamic nuclei connect with the globus pallidus. For conductivity in basal ganglia of the rat see Oorschot (1996) J. Comp. Neurol. 366:580–599.

In a preferred embodiment, the administration site is the striatum of the brain, in particular the caudate putamen. Injection into the putamen can label target sites located in various distant regions of the brain, for example, the globus pallidus, amygdala, subthalamic nucleus or the substantia nigra. Transduction of cells in the pallidus commonly causes retrograde labelling of cells in the thalamus. In a preferred embodiment the (or one of the) target site(s) is the substantia nigra.

In another preferred embodiment the vector system is injected directly into the spinal cord. This administration site accesses distal connections in the brain stem and cortex.

Within a given target site, the vector system may transduce a target cell. The target cell may be a cell found in nervous tissue, such as a neuron, astrocyte, oligodendrocyte, microglia or ependymal cell. In a preferred embodiment, the target cell is a neuron, in particular a TH positive neuron.

The vector system is preferably administered by direct injection. Methods for injection into the brain (in particular the striatum) are well known in the art (Bilang-Bleuel et al (1997) Proc. Acad. Nati. Sci. USA 94:8818–8823; Choi-Lundberg et al (1998) Exp. Neurol.154:261–275; Choi-Lundberg et al (1997) Science 275:838–841; and Mandel et al (1997) ) Proc. Acad. Natl. Sci. USA 94:14083–14088). Stereotaxic injections may be given.

As mentioned above, for transduction in tissues such as the brain, it is necessary to use very small volumes, so the viral preparation is concentrated by ultracentrifugation. The resulting preparation should have at least $10^8$ t.u./ml, preferably from $10^8$ to $10^{10}$ t.u./ml, more preferably at least $10^9$ t.u./ml. (The titer is expressed in transducing units per ml (t.u./ml) as titred on a standard D17 cell line). It has been found that improved dispersion of transgene expression can be obtained by increasing the number of injection sites and decreasing the rate of injection (Horellou and Mallet (1997)

as above). Usually between 1 and 10 injection sites are used, more commonly between 2 and 6. For a dose comprising 1–5×109 t.u./ml, the rate of injection is commonly between 0.1 and 10 µl/min, usually about 1 µl/min.

In another preferred embodiment the vector system is administered to a peripheral administration site. The vector may be administered to any part of the body from which it can travel to the target site by retrograde transport. In other words the vector may be administered to any part of the body to which a neuron within the target site projects.

The "periphery" can be considered to be all part of the body other than the CNS (brain and spinal cord). In particular, peripheral sites are those which are distant to the CNS. Sensory neurons may be accessed by administration to any tissue which is innervated by the neuron. In particular this includes the skin, muscles and the sciatic nerve.

In a highly preferred embodiment the vector system is administered intramuscularly. In this way, the system can access a distant target site via the neurons which innervate the innoculated muscle. The vector system may thus be used to access the CNS (in particular the spinal cord), obviating the need for direct injection into this tissue. There is thus provided a non-invasive method for transducing a neuron within the CNS. Muscular administration also enables multiple doses to be administered over a prolonged period.

Another advantage with this system is that it is possible to target particular groups of cells (e.g. sets of neurons), or a particular neural tract by choosing a particular administration site.

In a preferred embodiment, the vector system is used to transduce a neuron which innervates (directly or indirectly) the administration site. The target neuron may, for example, be a motoneuron or a sensory neuron.

Sensory neurons may also be accessed by administration to any tissue which is innervated by the neuron. In particular this includes the skin and the sciatic nerve. Where a patient is suffering from pain (in particular slow, chronic pain), the particular sensory neuron(s) involved in transmitting the pain may be targetted by administration of the vector system directly into the area of pain.

The lentiviral vector is advantageously as in U.S. Pat. Nos. 6,312,683, 6,312,682 or in other patent documents (e.g., applications) incorporated herein by reference wherein the assignee or applicant (e.g., on PCT and UK applications) is Oxford Biomedica, such as UK application serail No 0024550.6 and PCT/GB01/04433, which can also be sources for additional vectors or additional coding sequences to be employed in the practice of the invention, e.g., additional vectors encoding Tyrosine Hydroxylase, GTP-cyclohydrolase I, Aromatic Amino Acid Dopa Decarboxylase and Vesicular Monoamine Transporter 2 (VMAT2) to be employed in the practice of the invention or for coding sequences for Tyrosine Hydroxylase, GTP-cyclohydrolase I, Aromatic Amino Acid Dopa Decarboxylase and Vesicular Monoamine Transporter 2 (VMAT2) to be expressed with the growth factor, e.g., GDNF by the lentiviral vector.

Thus, the present invention comprehends that the administered vector, e.g., the administered lentiviral vector, can include and express additional nucleic sequences, such as nucleic acid sequences encoding one or more other members of the GDNF-family of neurotrophic factors, e.g., neurturin, persphin, neublastin, artemin; and/or the administered vector, e.g., lentiviral vector, can contain and express one or more other nucleotide sequences encoding expression products suitable for treating a neurdegenerative disorder, such as Tyrosine Hydroxylase, GTP-cyclohydrolase I, Aromatic Amino Acid Dopa Decarboxylase and Vesicular Monoamine Transporter 2 (VMAT2), preferably nucleic acid sequences encoding Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2. These other nucleotide sequences may also encode proteins such as growth factors, e.g., NGF and/or BDNF, and antibodies.

Additionally or alternatively, the invention comprehends that the administered vector, e.g., lentiviral vector, encoding the growth factor, e.g., GDNF, can be administered with one or more additional vectors containing one or more additional nucleic acid sequences, such as nucleic acid sequences encoding one or more other members of the GDNF-family of neurotrophic factors, e.g., neurturin, persphin, neublastin, artemin, and/or other nucleotide sequences encoding expression products suitable for treating a neurdegenerative disorder, such as Tyrosine Hydroxylase, GTP-cyclohydrolase I, Aromatic Amino Acid Dopa Decarboxylase and Vesicular Monoamine Transporter 2 (VMAT2), preferably encoding Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2. These other nucleotide sequences may also encode proteins such as growth factors and antibodies. The one or more additional vector can be any suitable vector such as an adenovirus or lentiviral vector; and, it is presently preferred and considered advantageous that the additional vector be a lentiviral vector, as AAV and adenovirus systems, as herein further discussed, do not obtain the enhanced effects observed with the lentiviral-growth factor, e.g., lentiviral-GDNF of the present invention. "Administration with" the lentiviral vector encoding the growth factor, e.g., GDNF, can be through simultaneous administration, e.g., the vectors are admixed in a single formulation that is administered, or via sequential or concomitant administration of the vectors or formulations containing the vectors.

When a vector genome such as a lentiviral or retroviral vector genome comprises two or more nucleic acid sequences (also known as nucleotide sequences of interest or NOIs), it is advantageous that they are operably linked by one or more Internal Ribosome Entry Site(s), e.g., a genome, advantageously a lentiviral genome, comprising three or more NOIs operably linked by two or more Internal Ribosome Entry Site(s) wherein preferably each NOI is useful in the treatment of a neurodegenerative disorder and at least one of the NOIs is a growth factor such as GDNF.

The invention also relates to vector systems, advantageously lentiviral vector systems, used in the methods of the invention, such as a lentiviral vector system which is capable of delivering an RNA genome to a recipient cell, wherein the genome is longer than the wild type genome of the lentivirus, e.g., an EIAV vector system; again, as discussed in documents herein assigned to Oxford Biomedica or wherein Oxford Biomedica is the named applicant, and with the vector expressing a growth factor such as GDNF, e.g., human GDNF, or a variant, homolog, analog or derivative thereof.

According to further aspects of the invention relates to:
  a method for producing a lentiviral particle which comprises introducing such a viral genome into a producer cell;
  a viral particle produced by such a system or method;
  a pharmaceutical composition comprising such a genome, system or particle;

the use of such a genome, system or particle in the manufacture of a pharmaceutical composition to treat and/or prevent a disease;

a cell which has been transduced with such a system;

a method of treating and/or preventing a disease by using such a genome, system, viral particle or cell;

Thus, the invention provides pharmaceutical compositions comprising the lentiviral vector or the lentiviral vector and other vector(s) employed in the methods of the invention, as well as kits for preparing such compositions (e.g., the lentiviral vector or the lentiviral vector and the other vector(s) in one or more containers and pharmaceutically acceptable excipient, carrier, diluent, adjuvant, and the like in one or more additional containers, wherein said containers can be provided in one or more packages, for instance, packaged together or separately, and optionally including instructions for admixture and/or administration).

The invention can also relate to a bicistronic cassette comprising a nucleotide sequence capable of encoding the growth factor, e.g., GDNF such as human GDNF or an analog, homolog, variant or derivative thereof, and an additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein, operably linked by one or more IRES(s). The invention likewise can also relate to tricistronic cassettes comprising a nucleotide sequence capable of encoding the growth factor, e.g., GDNF such as human GDNF or an analog, homolog, variant or derivative thereof, and a first additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein and a second additional nucleic acid sequence, e.g., an additional nucleic acid sequences encoding one or more other GDNF-family of neurotrophic factors or useful in treating or preventing neurodegenerative disease, such as those above-mentioned or otherwise mentioned herein or in documents incorporated by reference herein, operably linked by two or more IRES(s). Further cassettes are envisioned by the invention.

In addition, it is again noted that while herein text may mention employing nucleotide sequences capable of encoding one or more other GDNF-family of neurotrophic factors, e.g., as additional sequences in lentiviral vectors such as lentiviral-growth factor, e.g., lentiviral-GDNF vectors, or in additional vectors administered with lentiviral vectors such as lentiviral-growth factor, e.g., lentiviral-GDNF vectors, such embodiments are not presently preferred because, as discussed below, work involving lentiviral-GDNF-family-gene-neublastin/artemin reported in the literature has not been reproducible.

Thus, lentiviral vectors, such as those in Oxford Biomedica patents and patent applications, and vectors for retrograde transport, as in Oxford Biomedica patents and/or patent applications, are advantageous for expression in vivo of a growth factor such as GDNF, e.g., human GDNF or a homolog, variant, analog or derivative thereof; for instance, for treatment, prevention and the like of a neurodegenerative disorder or malady or disease or symptoms thereof, such as Parkinson's disease.

Accordingly, the neurodegenerative disease can be Parkinson's disease; and, the invention comprehends methods for treating or preventing Parkinson's disease or symptoms thereof and compositions therefor and kits for preparing such compositions.

The treating of Parkinson's disease can be by prevention of nigrostriatal degeneration and/or induction of nigrostriatal regeneration and/or reversal of motor deficits.

And, the growth factor expression, e.g., GDNF such as human GDNF or an analog, homolog, derivative or variant thereof, can be for up to 8 months.

These and other embodiments are disclosed or are obvious from and encompassed by, the following Detailed Description.

BRIEF DESCRIPTION OF FIGURES

The patent file contains at least one photograph executed in color. Copies of this patent with color photographs will be provided by the U.S. Patent and Trademark Office upon request and payment of the necessary fee.

The following Detailed Description, given to describe the invention by way of example, but not intended to limit the invention to specific embodiments described, may be understood in conjunction with the accompanying Figures, incorporated herein by reference, in which:

FIG. 1 (FIGS. 1A–E) shows: (A) Dense GDNF immunoreactivity within the head of the caudate nucleus and putamen in a lenti-GDNF-treated aged monkey. (B) In contrast, no GDNF immunoreactivity was observed in these regions in a lenti-βGal-treated animal. IC, internal capsule. (C) Dense GDNF immunoreactivity was observed within the midbrain of a lenti-GDNF-treated animal. (D) GDNF immunoreactivity within the forebrain of a lenti-GDNF-treated monkey. The staining within the putamen (Pt) is from an injection site. The staining within both segments of the globus pallidus (GPe and GPi) is the result of anterograde transport. (E) Anterogradely transported GDNF was also seen in the substantia nigra pars reticulate. Note that the holes in the tissue sections were made post mortem for HPLC analysis. Asterisk in (E) represents a lenti-GDNF injection site (CP, cerebral peduncle). Scale bar in (D) represents 1600 $\mu$m for panels A, B, and D; 1150 $\mu$m for panel C, and 800 $\mu$m for panel E.

FIG. 2 (FIGS. 2A–D) shows: PET scan data evaluating the influence of lenti-GDNF on FD uptake in (A and B) intact aged monkeys and (C and D) young adult MPTP-treated monkeys. (A) FD uptake did not change from baseline to 3 months after lentivirus injection in lenti-βGal-treated aged monkeys. (B) In contrast, lenti-GDNF injections manifested increased FD uptake on the side of GDNF expression relative to preoperative levels in aged monkeys. $K_i$ values (per minute) for the striatum are as follows: (left side) lenti-βGal preoperative 0.0068±0.0001, lenti-βGal postoperative 0.0062±0.0002; (right side) lenti-βGal preoperative 0.0068±0.0002, lenti-βGal postoperative 0.0065±0.0001; (left side) lenti-GDNF preoperative 0.0072±0.0005, lenti-GDNF postoperative 0.0068±0.0003; (right side) lenti-GDNF preoperative 0.0076±0.0004, lenti-GDNF postoperative 0.0081±0.0003. (C) After MPTP lesions, a comprehensive loss of FD uptake was seen within the right striatum of lenti-βGal-treated young adult monkeys. (D) In contrast, FD uptake was enhanced in lenti-GDNF-treated monkeys. $K_i$ values (per minute) for the striatum are as follows: lenti-βGal left, 0.0091±0.0004; lenti-βGal right, 0.0017±0.0005; lenti-GDNF left, 0.0084±0.0004; lenti-GDNF right, 0.0056±0.0018.

FIG. 3 (FIGS. 3A–F) shows: (A) Section stained for TH immunoreactivity through the anterior commissure illustrating the increase in TH immunoreactivity within the right caudate nucleus and putamen after lenti-GDNF delivery to aged monkeys. (B) Symmetrical and less intense staining for TH immunoreactivity in a monkey injected with lenti-βGal. (C) There were greater numbers and larger TH-immunoreactive neurons within the substantia nigra of a lenti-GDNF-treated animal relative to (D) a lenti-βGal-treated monkey. (E) Lenti-GDNF-treated aged monkeys displayed increased TH mRNA relative to (F) lenti-βGal-treated monkeys in the SN. Scale bar in (F) represents 4500 μm for panels 250 μm for panels (C) and (D) and 100 μm for panels (E) and (F)

FIG. 4 (FIGS. 4A–F) shows: Plots of quantitative data illustrating enhanced nigrostriatal function in lenti-GDNF-treated aged monkeys. Solid bars denote lenti-βGal-treated monkeys; hatched bars indicate lenti-GDNF-treated monkeys. GDNF expression was limited to the right striatum and nigra. $P<0.01$;*$P<0.001$.

FIG. 5 (FIGS. 5A–B) shows: After MPTP-treatment, lenti-GDNF-injected monkeys displayed functional improvement on (A) the clinical rating scale and (B) the hand-reach task. All tests were performed 3 weeks per month (see Emborg et al. 1998). On the clinical rating scale, monkeys were matched into groups based upon the post-MPTP score. For the hand-reach task, each symbol represents the mean of three sessions per week for the left hand. Monkeys were not tested on this task during the week between MPTP and lentivirus injection. *$P<0.05$ relative to lenti-βGal.

FIG. 6 (FIGS. 6A–H) show: (A and B) Low-power dark-field photomicrographs through the right striatum of TH-immunostained sections of MPTP-treated monkeys treated with (A) lenti-βGal or (B) lenti-GDNF. (A) There was a comprehensive loss of TH immunoreactivity in the caudate and putamen of lenti-βGal-treated animal. In contrast, near normal level of TH immunoreactivity is seen in lenti-GDNF-treated animals. Low-power (C and D) and medium-power (E and F) photomicrographs of TH-immunostained section through the substantia nigra of animals treated with lenti-βGal (C and E) and lenti-GDNF (D and F). Note the loss of TH-immunoreactive neurons in the lenti-βGal-treated animals on the side of the MPTP-injection. TH-immunoreactive sprouting fibers, as well as a supranormal number of TH-immunoreactive nigral perikarya are seen in lenti-GDNF-treated animals on the side of the MPTP injection. (G and H) Bright-field low-power photomicrographs of a TH-immunostained section from a lenti-GDNF-treated monkey. (G) Note the normal TH-immunoreactive fiber density through the globus pallidus on the intact side that was not treated with lenti-GDNF. (H) In contrast, an enhanced network of TH-immunoreactive fibers is seen on the side treated with both MPTP and lenti-GDNF. Scale bar in (G) represents the following magnifications: (A), (B), (C), and (D) at 3500 μm; (E), (F), (G), and (H) at 1150 μm.

FIG. 7 (FIGS. 7A–D) shows: (A through D) Quantification of lenti-GDNF's trophic effects on nigral neuronal number, volume, TH mRNA and striatal TH immunoreactivity in MPTP-treated monkeys. ***$P<0.001$ significant decreases relative to intact side; ttt denotes significant increases relative to the intact side.

FIG. 8 (FIGS. 8A–E) shows: Lenti-GDNF injections result in a minimal immune response 3 months after lentivirus injection. CD45-immunostained sections from (A and B) aged monkeys injected with lenti-GDNF or (C and D) MPTP-treated monkeys. (A) Low-power photomicrograph illustrating a minor CD45 reaction in this animal. The area boxed in (A) is seen at higher magnification in (B), where a cell with microglial morphology can be seen. (C and D) Even less CD45-ir is seen in other cases in sections through the needle tract. (E) In contrast, robust CD-45 is seen in a brain section from a human patient with Alzheimer's disease that served as a positive control for the immunohistochemical procedure. Scale bar in (A) represents the following magnifications: (A) and (C), 1800 μm; (B), 90 μm; (D), 180 μm; (E), 540 μm.

FIG. 9 (FIGS. 9A–D) shows: Long-term gene expression revealed in GDNF-immunostained sections from monkey receiving lenti-GDNF injections and killed 8 months later. Extensive GDNF-ir is seen within the right (A) caudate nucleus and (B) putamen. Holes in the tissue sections were made postmortem for GDNF ELISA analysis. (C and D) illustrate the neuronal retrograde GDNF-ir and fiber-anterograde labeling within the right substantia nigra that results from these injections. (E) GDNF ELISA data illustrating the levels of GDNF produced in vivo 8 months after lenti-GDNF injections. (IC, internal capsule). Scale bar in (A) represents the following magnifications: (A) and (B), 600 μm; (C),150 μm, (D), 60 μm.

DETAILED DESCRIPTION

Glial cell line-derived neurotrophic factor (GDNF) has potent trophic effects on dopaminergic nigral neurons (Bjorklund et al. 1997, Tseng et al. 1997, Lapchak et al. 1997, Gash et al. 1998, Kearns et al. 1995, Gash et al. 1996), suggesting that this factor could provide neuroprotection in patientswith early PD.

Intraventricular administration of GDNF failed to improve clinical function or prevent nigrostriatal degeneration in a patient with PD, and this failure resulted from an ineffective delivery method (Kordower et al. 1999a), demonstrating that actual tests with a true animal model, such as a primate is useful.

Gene therapy is a powerful means to deliver trophic molecules to the central nervous system in a site-specific manner.

Robust transfer of marker and therapeutic genes has recently been demonstrated in the rodent and nonhuman primate brain with the use of a lentiviral vector (Naldini et al. 1996, Takahashi et al. 1999, Mitrophanous et al. 1999, Wang et al. 1999, Deglon et al. 2000, Kordower et al. 1999b). The transgene expression is long-term and nontoxic. Using two different nonhuman primate models of PD, we examined whether lentiviral-mediated delivery of GDNF could reverse the cellular and behavioral changes associated with nigrostriatal degeneration in primates. For the first model, we chose nonlesioned aged monkeys that displayed a slow progressive loss of dopamine within the striatum and tyrosine hydroxylase (TH) within the substantia nigra without frank cellulardegeneration (Emborg et al. 1998). These aged monkeys demonstrate changes within the nigrostriatal system that model some of the incipient cellular changes seen in early PD (Kastner et al. 1993). In the second model, young adult monkeys received unilateral intracarotid injections of 1-methyl-4-phenyl-1,2,3,6-tetrahydropyridine (MPTP) to induce extensive nigrostriatal degeneration, resulting in a behavioral syndrome characterized by robust motor deficits.

An first aspect of the invention involves retroviral and lentiviral vector genomes.

The concept of using viral vectors for gene therapy is well known (Verma and Somia (1997) Nature 389:239–242).

There are many retroviruses. For the present application, the term "retrovirus" includes: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758–763).

Lentiviruses also belong to the retrovirus family, but they can infect both dividing and non-dividing cells (Lewis et al (1992) EMBO J. 3053–3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found at http://hiv-web.lanl.gov. Details of EIAV variants may be found through ncbi.nlm.nih.gov.

Lentiviruses that are the subject of patents and patent publications and patent applications of Oxford Biomedica are advantageously employed in the practice of the invention.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes which code for proteins other than gag, pol and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Another aspect of the invention involves delivery systems.

Retroviral vector systems have been proposed as a delivery system for inter alia the transfer of a NOI to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158:1–24).

A recombinant retroviral vector particle is capable of transducing a recipient cell with an NOI. Once within the cell the RNA genome from the vector particle is reverse transcribed into DNA and integrated into the DNA of the recipient cell.

As used herein, the term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques. Preferably the genome comprises a psi region (or an analogous component which is capable of causing encapsidation).

The viral vector genome is preferably "replication defective" by which we mean that the genome does not comprise sufficient genetic information alone to enable independent replication to produce infectious viral particles within the recipient cell. In a preferred embodiment, the genome lacks a functional env, gag or pol gene.

The viral vector genome may comprise some or all of the long terminal repeats (LTRs). Preferably the genome comprises at least part of the LTRs or an analogous sequence which is capable of mediating proviral integration, and transcription. The sequence may also comprise or act as an enhancer-promoter sequence.

The viral vector genome of the first aspect of the invention may be provided as a kit of parts. For example, the kit may comprise (i) a plasmid or plasmids containing the NOI(s) (nucleotide(s) of interest, such as GDNF alone or in combination with other NOIs) and optionaly IRES sequence(s) (e.g., if additional NOIs are present in a vector, such as a lentiviral vector, in addition to GDNF); and (ii) a retroviral genome construct with suitable restriction enzyme recognition sites for cloning the NOI(s) and any IRES(s) into the viral genome.

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell.

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome according to the first aspect of the invention (having a psi region) is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line comprising a viral vector genome of the first aspect of the invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method.

The components of the viral system which are required to complement the vector genome may be present on one or more "producer plasmids" for transfecting into cells.

The present invention also provides a vector system, comprising
(i) a viral genome according to the first aspect of the invention;
(ii) a nucleotide sequence coding for lentiviral gag and pol proteins;
(iii) nucleotide sequences encoding other essential viral packaging components not encoded by the nucleotide sequence of ii). In a preferred embodiment, the nucleotide sequence of (iii) is capable of encoding an env protein. The present invention also provides a cell transfected with such a vector system and a retroviral vector particle produced by such a cell. Preferably the gag-pol sequence is codon optimised for use in the particular producer cell.

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts which can be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasmids. By cotransfection of the genome together with the producer plasmid(s), the necessary components should be provided for the production of infectious viral particles.

Alternatively, the complementary nucleotide sequence(s) may be stably present within a packaging cell line that is included in the kit.

The present invention also relates to a lentiviral vector system which is capable of delivering an RNA genome to a recipient cell, wherein the genome is longer than the wild type genome of the lentivirus. The vector system may, for example, be an EIAV vector system.

Preferably the RNA genome of the vector system has up to 5%, more preferably up to 10% or even up to 30% more bases than the wild-type genome. Preferably the RNA genome is about 10% longer than the wild-type genome. For example, wild type EIAV comprises an RNA genome of approximately 8 kb. An EIAV vector system of the present invention may have an RNA genome of up to (preferably about) 8.8 kb.

Preferably the retroviral vector system of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene. Yu et al., (1986) PNAS 83: 3194–98; Marty et al., (1990) Biochimie 72: 885–7; Naviaux et al., (1996) J. Virol. 70: 5701–5; Iwakuma et al., (1999) Virol. 261: 120–32; Deglon et al., (2000) Human Gene Therapy 11: 179–90.

Preferably a recombinase assisted mechanism is used which facilitates the production of high titre regulated lentiviral vectors from the producer cells of the present invention.

As used herein, the term "recombinase assisted system" includes but is not limited to a system using the Cre recombinase/loxP recognition sites of bacteriophage P1 or the site-specific FLP recombinase of *S. cerevisiae* which catalyses recombination events between 34 bp FLP recognition targets (FRTs).

The site-specific FLP recombinase of *S. cerevisiae* which catalyses recombination events between 34 bp FLP recognition targets (FRTs) has been configured into DNA constructs in order to generate high level producer cell lines using recombinase-assisted recombination events (Karreman et al (1996) NAR 24:1616–1624). A similar system has been developed using the Cre recombinase/loxP recognition sites of bacteriophage P1 (Vanin et al (1997) J. Virol 71:7820–7826). This was configured into a lentiviral genome such that high titre lentiviral producer cell lines were generated.

By using producer/packaging cell lines, it is possible to propagate and isolate quantities of retroviral vector particles (e.g. to prepare suitable titres of the retroviral vector particles) for subsequent transduction of, for example, a site of interest (such as adult brain tissue). Producer cell lines are usually better for large scale production or vector particles.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392–8396).

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line which has been screened and selected for high expression of a marker gene. Such cell lines support high level expression from the retroviral genome. The term "derived producer cell line" is used interchangeably with the term "derived stable producer cell line" and the term "stable producer cell line.

Preferably the derived producer cell line includes but is not limited to a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as codon optimised gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266), and utilised to create producer cell lines for the production of retroviral vector particles. As already mentioned, a summary of the available packaging lines is presented in "Retroviruses" (as above).

Also as discussed above, simple packaging cell lines, comprising a provirus in which the packaging signal has been deleted, have been found to lead to the rapid production of undesirable replication competent viruses through recombination. In order to improve safety, second generation cell lines have been produced wherein the 3'LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example between the regions of overlap in the gag-pol and env open reading frames.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a primate or human cell line, such as for example: HEK293, 293-T, TE671, HT1080.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

It is highly desirable to use high-titre virus preparations in both experimental and practical applications. Techniques for increasing viral titre include using a psi plus packaging signal as discussed above and concentration of viral stocks.

As used herein, the term "high titre" means an effective amount of a retroviral vector or particle which is capable of transducing a target site such as a cell.

As used herein, the term "effective amount" means an amount of a regulated retroviral or lentiviral vector or vector particle which is sufficient to induce expression of the NOIs at a target site.

A high-titre viral preparation for a producer/packaging cell is usually of the order of $10^5$ to $10^7$ retrovirus particles per ml. For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml. (The titer is expressed in transducing units per ml (t.u./ml) as titred on a standard D17 cell line). Other methods of concentration such as ultrafiltration or binding to and elution from a matrix may be used.

The expression products encoded by the NOIs may be proteins which are secreted from the cell. Alternatively the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighbouring or distant (e.g. metastatic), which possess a common phenotype. Zennou et al., (2000) Cell 101: 173; Folleuzi et al., (2000) Nat. Genetics 25: 217; Zennou et al., (2001) Nat. Biotechnol. 19: 446.

The presence of a sequence termed the central polypurine tract (cPPT) may improve the efficiency of gene delivery to non-dividing cells. This cis-acting element is located, for example, in the EIAV polymerase coding region element. Preferably the genome of the present invention comprises a cPPT sequence.

Preferably the viral genome comprises a post-translational regulatory element. For example, the genome may comprise an element such as the woodchuck hepatitis virus posttranscriptional regulatory element (WPRE). Zufferey et al., (1999) J. Virol. 73: 2886; Barry et al., (2001) Human Gene Therapy 12: 1103.

In addition, or in the alternative, the viral genome may comprise a translational enhancer.

The NOIs may be operatively linked to one or more promoter/enhancer elements. Transcription of one or more NOIs may be under the control of viral LTRs or alternatively promoter-enhancer elements. Preferably the promoter is a strong viral promoter such as CMV, or is a cellular constitutive promoter such as PGK, beta-actin or EF1alpha. The promoter may be regulated or tissue-specific. Such promoters may be selected from genes such as neurofilaments, nestin, parkin, dopamine receptors, tyrosine hydroxylase. Such promoters may also contain neurorestrictive suppressor sequences such as that found in the mu-opoid receptor gene. In a preferred embodiment, the promoter may be glial-specific or neuron-specific. The control of expression can also be achieved by using such systems as the tetracycline system that switches gene expression on or off in response to outside agents (in this case tetracycline or its analogues). See also Bujard et al., U.S. Pat. Nos. 6,004,941 and 5,814,618 with respect to regulating gene expression.

It may be advantageous to control the expression of GDNF or other therapeutic molecule. It is possible to control gene expression with an exogenous signal (a "gene-switch"). There have been numerous methods proposed to achieve that appear to function quite well in animal models of various kinds (Gossen, M., Freundlieb,S., Bender, G., Muller,G., Hillen,W. and Bujard,H. 'Transcriptional activation by tetracyclines in mammalian cells" Science 1995 268:1766–1769; Rivera,V. M., Clackson,T., Natesan,S., Pollock,R., Amara,J. F., Kenen,T., Magari,R. M. Phillips,T. Courage,N. L. Cerasoli,F.,Jr., Holt,D. A. and Gilman,M. "A humanized system for pharmacological control of gene expression" Nature Medicine 1996 2:1028–1032; Abruzzese,R. V., Godin,D., Burcin,M., Mehta,V., French, M., Li,Y., O'Malley,B. W. and Nordstrom,J. L. "Ligand-dependent regulation of plasmid based transgene expression in vivo" Hum. Gene Ther. 1999 10:1499–1507; No D., Yao TP. and Evans R. M. "Ecdysone-inducible gene expression in mammalian cells and transgenic mice." Proc. Natl. Acad. Sci. USA. 1996 93:3346–3351; Yao,F. & Eriksson,E. "A novel tertacycline-inducible viral replication switch" Humans Gene Ther. (1999) 10:419–427).

In general these systems rely on the introduction of a gene for at least one exogenous "switch" protein, as part of the gene therapy, that is continuously expressed and is capable of sensing the presence of a specific ligand (normally a small molecule) that is otherwise inert when administered to animals or patients. This is in addition to the therapeutic gene. In the presence of the ligand the exogenous protein is activated to become either a positive or a negative transcription factor for the therapeutic gene expression.

These systems control levels of transgene expression so that toxicity can be avoided and physiologically and clinically appropriate levels of the transgene protein will be produced. The ability to achieve this in a clinically and regulatorily acceptable fashion will allow more effective therapies.

Most of the above systems rely on transcription control and the use of ligand alteration of protein receptor or transcription factor properties. However it is quite possible to control protein expression at the translational level depending on the nature of the RNA transcript. In addition it has been known for several years now that it is possible to select, from random pools, RNA sequences of 20 to 40 nucleotides, that bind quite tightly to a specific ligand used in the selection process (See A D Ellington and J W Szostak "In vitro selection of RNA molecules that bind specific ligands" Nature 1990 346: 818–822; R R White, B A Sullenger and C R Rusconi "Developing aptamers into therapeutics" J. Clin Invest. 2000 106: 929–934). Interestingly, the major applications seen for such observations has been the use of the RNA molecules as antagonists for various interactions occuring in cells, such as the HIV tat- TAR RNA interaction that facilitates HIV infection (White et al op.cit.).One publication has suggested using this mechanism as a way to control gene expression by inserting the aptamer into a message sequence then adding a cell permeable ligand for which the aptamer has been selected (G Werstuck and M R Green "Controlling Gene expression in living cells through small molecule-RNA interactions" Science (1998) 282:296–298 and WO00/20040). However the molecules proposed for use were either aminoglycoside antibiotics such as kanamycin and tobramycin or Hoechst dyes. Thus the system does not propose to use innocuous compounds for this purpose but rather compounds with known toxicities or that have no history of human use. This system thus is subject to issues described above. It also shows effects at concentration of drugs in the hundreds of micromolar to millimolar range. Typically this is the kind of concentration that is extremely difficult to reach in patient tissue or blood stream by oral administration of small molecule drugs.

However it is possible to avoid these problems by selecting from a large library of sequences, with many more rounds of selection (20 to 40), aptamers that bind to innocuous well-characterized compounds with a record of human use. Ideally these are orally available, with known pharmacokinetics with a T1/2>12 h. These compounds are selected to be able to enter the tissue where it is desired to control expression. For example, for neural tissue the known ability to cross the blood brain barrier is important. The aptamer sequence is then inserted in the gene, the expression of which is to be controlled, and the safe permeable molecule used to turn off protein expression as desired. Examples of such small drug molecules include prescription drugs such as tetracycline or doxycycline, but also many over the counter (OTC) drugs (see such as aspirin or other mild analgesics), or compounds on the FDA list of "generally recognized as safe" (GRAS) compounds (see fda.nov/cder/otc). Other examples are nicotine (normally used to quit smoking) and other nucleoside analogues, and various food additives including color dyes etc. If single aptamer sequences are responsive but only partially suppress expression, multiple copies can be inserted. The gene, the expression of which is to be controlled, can in general be delivered to animals and patients by any of the available viral or non-viral vector systems (See "The development of Human Gene Therapy T. Friedmann Ed., Cold Spring Harbor Laboratory Press, 1999). It can be used to control expression of a therapeutic gene, an accessory gene such as a selectable marker or expression of a viral protein of a viral vector. In the case of a viral vector this can also be used to create replicating vectors, the replication of which is controllable by administration of an outside agent.

Another aspect of the invention can involve pseudotyping.

In the design of retroviral vector systems it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841–847.

In a preferred embodiment of the present invention the vector system is pseudotyped with a gene encoding at least part of the rabies G protein. In a further preferred embodiment of the present invention the vector system is pseudotyped with a gene encoding at least part of the VSV-G protein.

It has been demonstrated that a lentivirus minimal system can be constructed from HIV, SIV, FIV, and EIAV viruses. Such a system requires none of the additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the delivery system used in the invention is devoid of at least tat and S2 (if it is an EIAV vector system), and possibly also vif, vpr, vpx, vpu and nef More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation or by replacement with other functional equivalent systems such as the MPMV system. As expression of the codon optimised gag-pol is REV independent, RRE can be removed from the gag-pol expression cassette, thus removing any potential for recombination with any RRE contained on the vector genome.

In a preferred embodiment the viral genome of the first aspect of the invention lacks the Rev response element (RRE).

In a preferred embodiment, the system used in the present invention is based on a so-called "minimal" system in which some or all of the additional genes have be removed.

The invention can also involve codon optimisation.

Codon optimisation has previously been described in WO99/41397. Different cells differ it their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation was based on highly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at hiv-web.lanl.cov. Details of EIAV clones may be found at the NCBI database: ncbi.nlm.nih.nov.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-termnial 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

The invention also involves NOIs.

The primary NOI involved in the invention is a nucleic acid molecule that encodes a growth factor such as GDNF, e.g., human GDNF or analogs, variants, derivatives, or homologs thereof.

In the present invention, the term NOI (nucleotide sequence of interest) includes any suitable nucleotide sequence, which need not necessarily be a complete naturally occurring DNA or RNA sequence. Thus, the NOI can be, for example, a synthetic RNA/DNA sequence, a codon optimised RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI(s), also referred to as "heterologous sequence(s)", "heterologous gene(s)" or "transgene(s)", may be any one or more of, for example, a selection gene(s), marker gene(s) and therapeutic gene(s).

The NOI may be a candidate gene which is of potential significance in a disease process. Thus the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group). The NOIs may also encode pro-drug activating enzymes.

Preferably the NOI is useful in the treatment of a neurodegenerative disorder.

More preferably the NOI is useful in the treatment of Parkinson's disease.

The NOI may encode a growth factor such as GDNF, e.g., human GDNF or an analog, homolog, derivative or variant thereof, or an enzyme involved in dopamine synthesis or storage. For example, the enzyme may be one of the following: Tyrosine Hydroxylase, GTP-cyclohydrolase I and/or Aromatic Amino Acid Dopa Decarboxylase. The sequences of all three genes are available: Accession Nos. X05290, U19523 and M76180 respecively.

Alternatively the NOI may encode the vesicular monoamine transporter 2 (VMAT2, Accession number L23205.1). In a preferred embodiment the viral genome comprises an NOI encoding GDNF alone or in combination with Aromatic Amino Acid Dopa Decarboxylase and an NOI encoding VMAT 2. Such a genome may be used in the treatment of Parkinson's disease, in particular in conjunction with peripheral administration of L-DOPA.

Alternatively the NOI may encode a growth factor capable of blocking or inhibiting degeneration in the nigrostriatal system. An example of such a growth factor is a neurotrophic factor. For example the NOI may encode glial cell-line derived neurotrophic factor (GDNF), brain-derived neurotrophic factor (BDNF), nerve growth factor (NGF), persephin growth factor, artemin growth factor, or neurturin growth factor, cilliary neurotrophic factor (CNTF), neurotrophin-3 (NT-3), neurotrophin-4 (NT-4), pantropic neurotrophin, and other related or unrelated neurotrophic factors. WO99/14235; WO00/18799; U.S. Pat. No. 6,090,778; U.S. Pat. No. 5,834,914; WO97/08196; U.S. Pat. No. 6,090,778; U.S. Pat. No. 5,288,622; WO92/05254; U.S. Pat. No. 6,037,320; WO95/33829; Baumgartner, B J and Shine, H D, J. Neurosci. 17: 6504–11 (1997). In a preferred embodiment, a lentiviral vector comprises one or more of these NOIs encoding neurotrophic factors.

Alternatively the NOI may encode a neuroprotective factor. In particular, the NOI(s) may encode molecules which prevent TH-positive neurons from dying or which stimulate regeneration and functional recovery in the damaged nigrostriatal system.

The NOI may encode all or part of the protein of interest ("POI"), or a mutant, homologue or variant thereof. For example, the NOI may encode a fragment of the POI which is capable of functioning in vivo in an analogous manner to the wild-type protein.

In a highly preferred embodiment, one of the NOIs comprises a truncated form of the TH gene, lacking the regulatory domain. Such an NOI avoids feed-back inhibition by dopamine which may limit expression of the full-length enzyme.

The term "mutant" includes POIs which include one or more amino acid variations from the wild-type sequence. For example, a mutant may comprise one or more amino acid additions, deletions or substitutions. A mutant may arise naturally, or may be created artificially (for example by site-directed mutagenesis).

Here, the term "homologue" means an entity having a certain homology with the NOI, or which encodes a protein having a degree of homology with the POI. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is –12 for a gap and –4 for each extension.

Calculation of maximum % homology therefore firstly requires the production of an optimal alignment, taking into consideration gap penalties. A suitable computer program for carrying out such an alignment is the GCG Wisconsin Besffit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However, for some applications, it is preferred to use the GCG Bestfit program. A new tool, called BLAST 2 Sequences is also available for comparing protein and nucleotide sequence (see FEMS Microbiol Lett 1999 174(2): 247–50; FEMS Microbiol Lett 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar—uncharged | C S T M |
| | | N Q |
| | Polar—charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another.

Preferably the NOI encodes a single POI (e.g., GDNF-such as human GDNF) or a mutant, homologue or variant thereof. In a highly preferred embodiment, the NOI does not encode a fusion protein. As used herein, the term "fusion protein" is used in its conventional sense to mean an entity which comprises two or more protein activities, joined together by a peptide bond to form a single chimeric protein. A fusion protein is encoded by a single polynucleotide driven by a single promoter.

The invention can also involve one or more internal ribosome entry site(s) (IRES)

The viral genome of the invention can comprise two or more NOIs (e.g., GDNF and another NOI expressing a POI useful in treating or preventing a neurodegenerative condition such as Parkinson's disease). In order for both of the NOIs to be expressed, there may be two or more transcription units within the vector genome, one for each NOI. However, it is clear from the literature that retroviral vectors achieve the highest titres and most potent gene expression properties if they are kept genetically simple (PCT/GB96/01230; Bowtell et al., 1988 J.Virol. 62, 2464; Correll et al., 1994 Blood 84, 1812; Emerman and Temin 1984 Cell 39, 459; Ghattas et al., 1991 Mol.Cell.Biol. 11, 5848; Hantzopoulos et al., 1989 PNAS 86, 3519; Hatzoglou et al., 1991 J.Biol.Chem 266, 8416; Hatzoglou et al., 1988 J.Biol.Chem 263, 17798; Li et al., 1992 Hum.Gen.Ther. 3, 381; McLachlin et al., 1993 Virol. 195, 1; Overell et al., 1988 Mol.Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197) and so it is preferable to use an internal ribosome entry site (IRES) to initiate translation of the second (and subsequent) coding sequence (s) in a poly-cistronic message (Adam et al 1991 J.Virol. 65, 4985).

Insertion of IRES elements into retroviral vectors is compatible with the retroviral replication cycle and allows expression of multiple coding regions from a single promoter (Adam et al (as above); Koo et al (1992) Virology 186:669–675; Chen et al 1993 J. Virol 67:2142–2148). IRES elements were first found in the non-translated 5' ends of picornaviruses where they promote cap-independent translation of viral proteins (Jang et al (1990) Enzyme 44: 292–309). When located between open reading frames in an RNA, IRES elements allow efficient translation of the downstream open reading frame by promoting entry of the ribosome at the IRES element followed by downstream initiation of translation.

A review on IRES is presented by Mountford and Smith (TIG May 1995 vol 11, No 5:179–184). A number of different IRES sequences are known including those from encephalomyocarditis virus (EMCV) (Ghattas, I. R., et al., *Mol. Cell.* Biol., 11:5848–5859 (1991); BiP protein [Macejak and Sarnow, Nature 353:91 (1991)]; the Antennapedia gene of Drosophila (exons d and e) [Oh, et al., *Genes & Development,* 6:1643–1653 (1992)] as well as those in polio virus (PV) [Pelletier and Sonenberg, *Nature* 334: 320–325 (1988); see also Mountford and Smith, TIG 11, 179–184 (1985)].

According to WO-A-97/14809, IRES sequences are typically found in the 5' non-coding region of genes. In addition to those in the literature they can be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

In order for the IRES to be capable of initiating translation of each NOI, it should be located between or prior to NOIs in the vector genome. For example, for a multicistronic sequence containing n NOIs, the genome may be as follows:

$$[(NOI_1\text{-}IRES_1] \ldots NOI_n = 1 \rightarrow n$$

For bi and tricistronic sequences, the order may be as follows:

$NOI_1$-$IRES_1$-$NOI_2$ $NOI_1$-$IRES_1$-$NOI_2$-$IRES_2$-$NOI_3$

Alternative configurations of IRESs and NOIs can also be utilised. For example transcripts containing the IRESs and NOIs need not be driven from the same promoter.

An example of this arrangement may be:

IRES$_1$-NOI$_1$-promoter-NOI$_2$-IRES$_2$-NOI$_3$.

In a preferred embodiment, in any construct utilising an internal cassette having more than one IRES and NOI, the IRESs may be of different origins, that is, heterologous to one another. For example, one IRES may be from EMCV and the other IRES may be from polio virus.

The invention can additionally involve other methods of expressing multiple genes from one vector.

Although IRESs are an efficient way to co-express multiple genes from one vector, other methods are also useful, and may be used alone or in conjunction with IRESs. These include the use of multiple internal promoters in the vector (Overell et al., Mol Cell Biol. 8: 1803–8 (1988)), or the use of alternate splicing patterns leading to multiple RNA species derived from the single viral genome that expresses the different genes. This strategy has previously been used by itself for two genes (Cepko et al. Cell 37: 1053 (1984)).

The invention can further involve transduced cells.

The present invention also relates to a cell which has been transduced with a vector system comprising a viral genome according to the first aspect of the invention.

Transduction with the vector system of the present invention may confer or increase the ability of the cell to produce catecholamines. It may, for example, confer or increase the ability of the cell to convert tyrosine to L-dopa and/or L-dopa to dopamine. Release of catecholamines can be measured by techniques known in the art, for example by using an electrochemical detector connected to an analytical cell. In addition of the catecholamines themselves, biproducts associated with catecholamine release (such as DOPAC, a specific degradation product of dopamine) may also be detected.

The cell may be transduced in vivo, in vitro or ex vivo. For example, if the cell is a cell from a mammalian subject, the cell may be removed from the subject and transduced ready for reimplantation into the subject (ex vivo transduction). Alternatively the cell may be transduced by direct gene transfer in vivo, using the vector system of the present invention in accordance with standard techniques (such as via injection of vector stocks expressing the NOIs). If the cell is part of a cell line which is stable in culture (i.e. which can survive numerous passages and can multiple in vitro) then it may be transduced in vitro by standard techniques, for example by exposure of the cell to viral supernatants comprising vectors expressing the NOIs.

The cell may be any cell which is susceptible to transduction. If the vector system is capable of transducing non-dividing cells (for example if it is a lentiviral system) then the cell may be a non-dividing cell such as a neuron.

In a preferred embodiment the transduced cell forms part of a genetically modified neuronal cell line. Such a cell line may, for example, be transplanted into the brain for the treatment of Parkinson's disease.

In a further embodiment the cell is a neuronal stem cell. Such a cell line may, for example, be transplanted into the brain for the treatment of Parkinson's disease.

In a further embodiment the cell is a cell in the striatum of a subject, such as a neuron or glial cell. Direct gene transfer in vivo to such a cell may, for example, convert it into a dopamine-producer cell.

The invention also involves cassettes.

The present invention also provides multicistronic cassettes comprising two or more NOIs operably linked by an IRES. These cassettes may be used in a method for producing the vector genome in a producer cell.

The present invention also provides an expression vector comprising such a cassette. Transfection of a suitable cell with such an expression vector should result in a cell which expresses each POI encoded by the NOI in the cassette. The present invention also provides such a transfected cell.

Cloning of the cassette into an expression vector and transfection of cells with the vector (to give expression of the cassette) can be carried out by techniques well known in the art (such as those described in Sambrook et al. (Molecular Cloning: A Laboratory Manual, 2nd Edition, Cold Spring Harbor Laboratory press (1989)), and other laboratory textbooks).

Preferably the cassette comprises a promoter. In a highly preferred embodiment the cassette is bicistronic or tricistronic and comprises the following elements:

Promoter-(NOI$_1$)-(IRES$_1$)-(NOI$_2$)

Promoter-(NOI$_1$)-(IRES$_1$)-(NOI$_2$)-(IRES$_2$)-(NOI$_3$)

In a particularly preferred embodiment the cassette is bicistronic and comprises an NOI encoding tyrosine hydroxylase (or a mutant, variant or homologue thereof) and an NOI encoding GDNF and/or GTP-cyclohydrolase I (or a mutant, variant or homologue thereof in either order. In another particularly preferred embodiment the cassette is bicistronic and comprises an NOI encoding GDNF and/or Aromatic Amino Acid Dopa Decarboxylase and an NOI encoding Vesicular Monoamine Transporter 2, in either order.

In another particularly preferred embodiment the cassette is tricistronic and comprises an NOI encoding GDNF and/or tyrosine hydroxylase (or a mutant, variant or homologue thereof), an NOI encoding GTP-cyclohydrolase I (or a mutant, variant or homologue thereof) and an NOI encoding Aromatic Amino Acid Dopa Decarboxylase (or a mutant, variant or homologue thereof) in any order.

In each of the foregoing cassettes, it is advantageous that at least GDNF (e.g., human GDNF or a mutant, variant, homolog, analog, derivative thereof) be present and at least one or more of the other recited NOIs.

The invention further comprehends pharmaceutical compositions.

The present invention also provides the use of a retroviral vector genone as defined herein in a pharmaceutical composition. The pharmaceutical composition may be used for treating an individual by gene therapy, wherein the composition comprises a therapeutically effective amount of a vector e.g., retroviral or lentiviral vector particle, according to the present invention.

The pharmaceutical composition may be used to treat a human or animal subject. Preferably the subject is a mammalian subject. More preferably the subject is a human. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Preferably the viral vector particles of the present invention are administered by injection into the caudate putamen or intracranially, e.g., to striatum and/or substantia nigra.

The invention also comprhends treating or preventing diseases or maladies or conditions or symptoms thereof.

The retroviral vector genome and vector particles of the present invention are particularly useful for the treatment and/or prevention of neurodegenerative diseases. Diseases which may be treated include, but are not limited to: Parkinson's disease; motor neuron disease, Huntington's disease and disorders of movement which are responsive to L-dopa, such as distonias. In particular, the present invention is useful in treating and/or preventing Parkinson's disease.

Treatment by gene therapy with vectors capable of delivering, for example, GDNF alone or in combination with any or all of TH, GTP-CH1 and optionally AADC or AADC and VMAT2, is likely to be particularly useful for the late stages of PD patients which do not respond significantly to L-dopa treatment. Treatment using AADC or AADC and VMAT2, in combination with L-dopa administered peripherally may also be useful for late stage PD patients.

The present invention will now be further described only by way of the following non-limiting examples, provided for illustration.

EXAMPLES

Example 1

Preparing Constructs and Formulations

The cDNA coding for a nuclear-localized β-galactosidase (LacZ) and the human GDNF containing a Kozak consensus sequence (a 636-bp fragment: position 1 to 151 and 1 to 485; GenBank accession numbers L19062 and L19063) were cloned in the SIN-W-PGK transfer vector (R. Zufferey et al., *Journal of Virology.* 77(12), 9873–9880 (1998), R. Zufferey, et al., *J. Virol.* 73, 2886 (1999)). The packaging construct and vesicular stomatis virus G protein (VSV-G) envelope used in this study were the PCMVDR8.92, PRSV-Rev, and the PMD.6 plasmids described previously; R. Zufferey, D. Nagy, R. J. Mandel, L. Naldini, D. Trono, *Nature Biotechnol.* 15, 871 (1997); A. F. Hottinger, M. Azzouz, N. Déglon, P. Gebischer, A. D. Zurn, *J. Neurosci.* 20, 5587 (2000). The viral particles were produced in 293T cells as previously described (Kordower et al. 1999b). The titers (3 to 5×10$^8$ TU/ml) of the concentrated LacZ-expressing viruses (200,000 and 250,000 ng p24/ml in experiment 1 and 450,000 ng p24/ml in experiment 2) were determined on 293T cells. The GDNF-expressing viral stocks were normalized for viral particles content using p24 antigen measurement.

Example 2

Administrations To Primates And Analyses Thereof

All experimentation was performed in accordance with NIH guidelines and institutional animal care approval. Level II Biosafety procedures were used. Under MRI guidance, each monkey received six stereotaxic injections of lenti-βGal or lenti-GDNF bilaterally into the caudate nucleus, putamen, and substantia nigra. Injections were made into the head of the caudate nucleus (10 μl), body of the caudate nucleus (5 μl), anterior putamen (10 μl), commissural putamen (10 μl), postcommissural putamen (5 μl), and substantia nigra (5 μl). Injections were made through a 10-μl Hamilton syringe connected to a pump at a rate of 0.5 μl/min. During the injection, the needle was raised 1 to 2 mm to better disperse the lentivirus through the intended target. The needle was left in place for an additional 3 min to allow the injectate to diffuse from the needle tip. The left side was injected 6 weeks before the right. During the first surgical session, there was a technical failure with the virus aggregating in the needle, which prevented its injection into the brain. This was confirmed at postmortem examination using GDNF-immunohistochemistry and β-Gal histochemistry. Thus, the left side served as an additional control for the right side.

In the first experiment, eight aged (approximately 25 years old) female rhesus monkeys received injections of lentiviral vectors encoding β-galactosidase (lenti-βGal; n=4) or GDNF (lenti-GDNF; n=4) targeted for the striatum and substantia nigra (as prepared in Example 1)and were killed 3 months later. Postmortem, all GDNF injectionswere localized to the caudate nucleus, putamen, and supranigral regions (in accordance with NIH guidelines as mentioned above), as revealed by standard staining procedures (GDNF immunohistochemistry was performed with a commercially available antibody (R&D Systems, Minneapolis, Minn.; 1:250), using the ABC method and nickel intensification. Deletion or substitution for the primary antibody served as controls. Under control conditions, no staining was observed.). All aged monkeys receiving lenti-GDNF displayed robust GDNF immunoreactivity within the right striatum (FIG. 1A) and substantia nigra (FIG. 1C). In contrast, no monkeys receiving lenti-βGal displayed specific GDNF immunoreactivity in the right striatum (FIG. 1B). Rather, these monkeys displayed robust expression of βGal similar to that reported previously (Kordower et al. 1999b). In lenti-GDNF-treated animals, GDNF immunoreactivity within the striatum was extremely dense and distributed throughout the neuropil (FIG. 1). When the primary antibody concentration was decreased to one-tenth of the standard, the intense striatal neuropil staining was diminished, and GDNF-immunoreactive perikarya were easily seen. Numerous GDNF-immunoreactive perikarya were also seen within the substantia nigra of lenti-GDNF-injected monkeys. Within the striatum and substantia nigra, Nissl-stained sections revealed normal striatal cytoarchitecture without significant cytotoxicity. Macrophages were occasionally observed within the needle tracts. Gliosis was similar across treatment groups and was principally confined to the regions immediately surrounding the needle tracts.

Lenti-GDNF injections resulted in marked anterograde transport of the trophic factor. Intense GDNF immunoreactivity was observed within fibers of the globus pallidus (FIG. 1D) and substantia nigra pars reticulata (FIG. 1E) after striatal injections. GDNF-containing fibers emanating from putaminal injection sites were seen coursing medially toward and into the globus pallidus (FIG. 1D). These staining patterns were clearly distinct from the injection site and respected the boundaries of the striatal target structures. In contrast, anterograde transport of βGal was not observed in lenti-βGal monkeys. This suggests that secreted GDNF, and not the virus per se, was anterogradely transported.

Aged monkeys underwent fluorodopa (FD) positron emission tomography (PET) before surgery and again just before being killed. (All procedures followed an overnight fast. After sedation with ketamine (10 to 15 mg/kg), the animal was intubated, and femoral angiocatheters were placed for tracer injection and blood sampling. Anesthesia was then maintained by 1 to 2% isofluorane for the remainder of the procedure. Carbidopa (2 to 3 mg/kg IV) was administered 30 min before the FD study. The animal was placed in a stereotaxic head holder constructed of materials compatible with PET scanning, and a transmission scan was acquired for correction of the emission data for attenuation. FD (185 MBq) was administered over 30 s and a 90-min three-dimensional dynamic emission scan started. The scan included 22 frames with durations increasing from 1 min initially to 5 min at the end. The bed was moved cyclically by the interplane distance between each pair of 5-min scans to give a net coronal sampling interval of 2.125 mm. Regions of interest (ROI) were placed on the caudate nucleus, putamen and occipital cortex in individual morphometric MR images coregistered with the FD image data. Cortical time courses were used as input functions to generate functional maps of the uptake rate constant $K_i$ by the modified graphical method (C. S. Patlak and R. G. Blasberg, *J. Cereb. Blood Flow Metab.* 5, 584 (1985).)

Striatal ROIs were transferred to the functional maps, and the $K_i$ values were evaluated as the ROI means for each structure.). Before treatment, all monkeys displayed symmetrical FD uptake in the caudate and putamen bilaterally (ratio: 1.02±0.02) (FIGS. 2A and 2B, left). Similarly, there was symmetrical (4% difference) FD uptake in all lentiβGal-treated monkeys after lentivirus injections (FIG. 2A, right). In contrast, FD uptake was significantly asymmetrical (27%) in lenti-GDNF-treated monkeys with greater uptake on the side of the GDNF expression (P<0.007; FIG. 2B, right). With respect to absolute values, lenti-βGal animals displayed a trend toward reduced FD uptake after treatment relative to baseline levels (P=0.06). Qualitatively, three of four lenti-GDNF-treated monkeys displayed clear increases in FD uptake on the treated side. This increase in uptake ($K_i$ value) between the groups just failed to reach statistical significance (P=0.06).

Within the striatum, lentiviral delivery of GDNF increased a number of markers of dopaminergic function (All monkeys were perfused with saline. The brain was removed, immersed in ice-cold saline for 10 min, and slabbed on a monkey brain slicer. Slabs through the head of the caudate and putamen were punched bilaterally with a 1-mm brain punch. These punches were processed for HPLC (Kordower et al. 1995). The tissue slabs were immersed in Zamboni's fixative. Stereological counts and volumes of TH-immunoreactive neurons were performed with Neuro-Zoom software using the optical dissector method for cell counting and the nucleator method for measuring neuronal volume (Emborg et al. 1998)). Optical density measurements were performed to assess the relative intensity of TH staining within the caudate nucleus and putamen (FIG. 3, A and B). On the left side where there was no lenti-GDNF expression, the intensity of TH immunoreactivity within the caudate nucleus and putamen was similar between groups (FIG. 3, A and B). In contrast, significant increases in optical density measures of TH immunoreactivity were seen in the right striatum of lenti-GDNF-infused monkeys (FIG. 3A) relative to lenti-βGal-treated animals (FIG. 3B) or the contralateral side (FIG. 3A). In this regard, there was a 44.1% and a 38.9% increase in optical density measures of TH immunoreactivity within the caudate nucleus and putamen, respectively (FIG. 4D). At the time of death, tissue punches were taken throughout the caudate nucleus and putamen of all monkeys. Relative to lenti-βGal-treated animals, measurement of dopamine (DA) and homovanillic acid (HVA) revealed significant increases in the right caudate nucleus (140% DA, P<0.001; 207% HVA, P<0.001) and putamen (47.2% DA, P<0.05; 128% HVA, P<0.01) in lenti-GDNF-treated aged monkeys (FIG. 4, E and F).

Lentiviral delivery of GDNF to aged monkeys resulted in an increase in the number of TH-immunoreactive neurons within the substantia nigra (FIG. 3, C and D). Regardless of the extent of GDNF immunoreactivity within the midbrain, the organization of TH-immunoreactive neurons was similar in all animals, and these neurons were not observed in ectopic locations within this locus. Stereological counts revealed an 85% increase in the number of TH-immunoreactive nigral neurons on the side receiving lentivirally delivered GDNF (FIG. 4A) relative to lenti-βGal-treated animals. On the side (left) that did not display GDNF immunoreactivity, lenti-GDNF-treated animals contained 76,929±4918 TH-immunoreactive neurons. This is similar to what was seen in lenti-βGal-infused animals (68,543±5519). Whereas lenti-βGal-infused monkeys contained 63,738±6094 TH-immunoreactive nigral neurons in the right side, lenti-GDNF-treated monkeys contained 118,170±8631 TH-immunoreactive nigral neurons in this hemisphere (P<0.001).

A similar pattern was seen when the volume of TH-immunoreactive substantia nigra neurons was quantified (FIG. 4B). TH-immunoreactive neurons from lenti-βGal- and lenti-GDNF-treated monkeys were similar in size in the left nigra where there was no GDNF expression (11,147.5±351 $\mu m^3$ and 11,458.7±379 $\mu m^3$, respectively). In contrast, a 35% increase in neuronal volume was seen on the GDNF-rich right side in lenti-GDNF-injected aged monkeys (lenti-βGal 10,707.5±333 $\mu m^3$; lenti-GDNF 16,653.7±1240 $\mu m^3$; P<0.001).

Although stereological counts of TH mRNA-containing neurons were not performed, there was an obvious increase in the number of TH mRNA-containing neurons within the right substantia nigra in lenti-GDNF-treated monkeys (FIG. 3E) compared with lenti-βGal-containing animals (FIG. 3F). With regard to the relative levels of TH mRNA expression within individual nigral neurons (the TH riboprobe was prepared as previously described (Kordower et al. 1999a). The probe was conjugated to 2 mM biotin-14-CTP (Gibco BRL/Life Technologies, Rockville, Md.), 1 μg Pvu I-linearized pBS-TH3', 5 mM DTT, 50 U RNasin, 4 U T3RNA polymerase, 0.5 mM CTP, and 0.25 mM of ATP, GTP, and UTP. Tissue was processed for immunohistochemistry by the ABC method using this probe as the primary antibody. Optical density measurements were performed using NIH Image.), the pattern of results was similar to that observed with TH-immunoreactive neuronal number and volume (FIG. 4C). On the left side, the optical density of TH mRNA within nigral neurons was similar between lenti-βGal- and lenti-GDNF-treated monkeys (78.28±2.78 and 80.58±2.5, respectively). In contrast, there was a significant (21.5%) increase in the optical density for TH mRNA in lenti-GDNF-treated monkeys (98.3±1.5) relative to lenti-βGal-treated monkeys (77.2±2.3) on the right side (P<0.01).

In the second experiment, 20 young adult rhesus were initially trained 3 days per week until asymptotic performance was achieved on a hand-reach task in which the time to pick up food treats out of recessed wells was measured (Emborg et al. 1998, Kordower et al. 1995). Each experimental day, monkeys received 10 trials per hand. Once per week, monkeys were also evaluated on a modified parkinsonian clinical rating scale (CRS). All monkeys then received an injection of 3 mg MPTP-HCl into the right carotid artery, initiating a parkinsonian state. One week later, monkeys were evaluated on the CRS. Only monkeys displaying severe hemiparkinsonism with the classic crooked arm posture and dragging leg on the left side continued in the study (n=10). It is our experience that monkeys with this behavioral phenotype display the most severe lesions neuroanatomically and do not display spontaneous recovery behaviorally (Kordower et al. 1995). On the basis of CRS scores, monkeys were matched into two groups of five monkeys, which received on that day lenti-βGal or lenti-GDNF treatment. Using magnetic resonance imaging (MRI) guidance, we gave all monkeys lentivirus injections into the caudate nucleus (n=2), putamen (n=3), and substantia nigra (n=1) on the right side using the same injection parameters as in experiment 1. One week later, monkeys began retesting on the hand-reach task three times per week for 3 weeks per month (Testing was performed during weeks 2 to 4 for month 1, and weeks 1 to 3 for months 2 and 3. Monkeys were not tested for the first week in month 1 to allow them time to recover from surgery. Testing was not performed for the final week of months 2 and 3 to allow for routine veterinary care (month 2) and transportation to the University of Wisconsin for PET scans (month 3).) For statistical analyses, the times for an individual week were combined into a single score. During the weeks of hand-reach testing, monkeys were also scored once per week on the CRS. Individuals blinded to the experimental treatment performed all behavioral assessments. Three months after lentivirus treatment, monkeys received a FD PET scan and were killed 24 to 48 hours later, and tissues were histologically processed as before.

Within 1 week after the lentivirus injections, one monkey from each group died. Necropsies from these animals revealed only the presence of mild necrosis from multifocal random hepatocellular coagulation. On account of these deaths, all remaining monkeys underwent detailed necropsies after death, and no significant abnormalities in any organs were seen.

Before MPTP treatment, all young adult monkeys scored 0 on the CRS. After MPTP, but before lentivirus injection, monkeys in the lenti-GDNF and lenti-βGal groups averaged 10.4±0.07 and 10.6±0.6, respectively, on the CRS (P>0.05). After lentivirus treatment, significant differences in CRS scores were seen between the two groups (Kolmogorov-Smirnov test, P<0.0001; FIG. 5A). CRS scores of monkeys receiving lenti-βGal did not change over the 3-month period after treatment. In contrast, CRS scores of monkeys receiving lenti-GDNF significantly diminished during the 3-month period after treatment. Scores began to decrease in the first month after lenti-GDNF treatment. However, statistically significant differences between lenti-GDNF and lenti-βGal were only discerned at posttreatment observations 6, 7, 8, and 9 (Kolmogorov-Smirnov test, P<0.04 for each comparison).

Lenti-GDNF-treated animals also improved performance on the operant hand-reach task. Under the conditions before MPTP administration, animals in both groups performed this task with similar speed (FIG. 5B). For the "unaffected" right hand, no differences in motor function were discerned for either group relative to performance before MPTP administration or to each other (P>0.05). In contrast, performance with the left hand was significantly improved in lenti-GDNF-treated animals relative to controls (P<0.05). After MPTP, all lenti-βGal-treated animals were severely impaired, with monkeys often not performing at all, or requiring more than the maximally allowed 30 s. In contrast, three of the four lenti-GDNF monkeys performed the task with the left hand at near-normal levels, whereas one lenti-GDNF-treated monkey was impaired and performed this task in a manner similar to the lenti-βGal-treated animals. Between groups, significant differences in performance were discerned on posttreatment tests 4, 6, 7, 8, and 9 (P<0.05 for each comparison).

Just before being killed, all monkeys underwent FD PET scans. Qualitatively, all lenti-βGal-treated monkeys displayed pronounced FD uptake in the left striatum and a comprehensive loss of FD uptake on the right side (FIG. 2C). In contrast, two of four lenti-GDNF-treated animals displayed robust and symmetrical FD uptake on both sides (FIG. 2D). The remaining two lenti-GDNF monkeys displayed reduced FD uptake on the right side, but with $K_i$ values 50 to 100% greater than lenti-βGal controls (FIG. 2). Quantitatively, no differences in FD uptake were observed between groups within the left striatum (P>0.05). In contrast, there was a significant (>300%) increase in FD uptake in lenti-GDNF-treated animals in the right striatum relative to lenti-pGal-treated animals (P<0.05). When the right striatum was subdivided, significant increases in FD uptake were only seen within the putamen of lenti-GDNF-treated animals (P<0.05).

After death, a strong GDNF-immunoreactive signal was seen in the caudate nucleus, putamen, and substantia nigra of all lenti-GDNF-treated, but none of the lenti-Gal-treated animals. The intensity and distribution of GDNF immunoreactivity was indistinguishable from what we observed in aged monkeys (see FIG. 1).

All lenti-βGal-treated monkeys displayed a comprehensive loss of TH immunoreactivity within the striatum on the side ipsilateral to the MPTP injection (FIG. 6A). In contrast, all lenti-GDNF-treated monkeys displayed enhanced striatal TH immunoreactivity relative to βGal controls (FIG. 6B). However, there was variability in the degree of striatal TH immunoreactivity in lenti-GDNF-treated animals and that variability was associated with the degree of functional recovery seen on the hand-reach task. Two lenti-GDNF-treated monkeys displayed dense TH immunoreactivity throughout the rostrocaudal extent of the striatum (FIG. 6B). In these monkeys, the intensity of the TH immunoreactivity was greater than that observed on the intact side. These two animals displayed the best functional recovery. A third lenti-GDNF-treated monkey also displayed robust functional recovery on the hand-reach task. However, the enhanced striatal TH immunoreactivity in this animal was limited to the post-commissural putamen. The fourth lenti-GDNF-treated monkey did not recover on the hand-reach task. Although putaminal TH immunoreactivity in this animal was still greater than controls, the degree of innervation was sparse and restricted to the medial post-commissural putamen.

Lenti-GDNF treatment enhanced the expression of TH-immunoreactive fibers throughout the nigrostriatal pathway. Unlike what was observed in aged monkeys, however, some TH-immunoreactive fibers in the striatum displayed a morphology characteristic of both degenerating and regenerating fibers. Large, thickened fibers could be seen coursing in an irregular fashion in these animals. Rostrally, these fibers appeared disorganized at times, with a more normal organization seen more caudally. TH-immunoreactive sprouting was also seen in the globus pallidus (FIG. 6, G and H), substantia innominata (FIG. 6, A and B), and lateral septum. These novel staining patterns were not immunoreactive for dopamine β-hydroxylase confirming the dopaminergic phenotype of this response.

Quantitatively, lenti-βGal-treated monkeys displayed significant decreases in the optical density of TH-immunoreactive fibers within the right caudate nucleus (71.5%; P<0.006; FIG. 7D) and putamen (74.3% P<0.0007; FIG. 7D) relative to the intact side. When analyzed as a group, TH optical density in the right caudate nucleus and putamen of lenti-GDNF-treated monkeys was significantly greater than that seen in lenti-βGal-treated monkeys (P<0.001 for both) and was similar to that seen on the intact side of these animals (P>0.05 for both).

All lenti-βGal-treated monkeys displayed a dramatic loss of TH-immunoreactive neurons within the substantia nigra on the side ipsilateral to the MPTP injection (FIG. 7A). In contrast, the nigra from all four of the lenti-GDNF-treated displayed complete neuroprotection (FIG. 7A), regardless of the degree of functional recovery. In lenti-βGal-treated monkeys, intracarotid injections of MPTP resulted in an 89% decrease in the number (FIG. 7A), and an 81.6% decrease in the density, of TH-immunoreactive nigral neurons on the side ipsilateral to the toxin injection (P<0.001). In contrast, lenti-GDNF-treated monkeys displayed 32% more TH-immunoreactive nigral neurons (P<0.001) and an 11% increase in TH-immunoreactive neuronal density (P<0.05) relative to the intact side. In lenti-βGal-treated animals, MPTP significantly reduced (32%) the volume of residual TH-immunoreactive nigral neurons on the lesion side relative to the intact side (P<0.001; FIG. 7B). In contrast, the volume of TH-immunoreactive neurons in lenti-GDNF-treated animals was significantly larger (44.3%) on the lesioned side relative to the intact side (P<0.001). Finally, the optical density of TH mRNA was quantified bilaterally in all animals (FIG. 7C). In lenti-βGal-treated animals, there was a significant decrease (24.0%) in the relative optical density of TH mRNA within residual neurons on the MPTP-lesioned side relative to the intact side (P<0.03). In contrast, lenti-GDNF-treated animals displayed a significant increase (41.7%) in relative optical density of TH mRNA relative to the intact side or lenti-βGal-treated animals (P<0.001).

Sections from all monkeys were stained for CD45, CD3, and CD8 markers to assess the immune response after lentiviral vector injection (See FIGS. 8 and 9). These antibodies are markers for activated microglia, T cells, and leukocytes including lymphocytes, monocytes, granulocytes, eosinophils, and thymocytes. Staining for these immune markers was weak, and often absent, in these animals. Mild staining for CD45 and CD8 was seen in two animals. Some CD45-immunoreactive cells displayed a microglial morphology. Other monkeys displayed virtually no immunoreactivity even in sections containing needle tracts.

Two additional intact young adult rhesus monkeys received lenti-GDNF injections into the right caudate and putamen and the left substantia nigra using the same injection protocol (See FIGS. 8 and 9). These animals were killed 8 months later and were evaluated by immunohistochemistry and enzyme-linked immunosorbent assay (ELISA) (Brain punches were homogenized in 150:1 buffer I [0.1M tris-buffered saline, pH 8.1, containing 1 mM EDTA, 1% aprotinin, 10 µg/ml leupeptin, 14 µg/ml pepstatin, 4 mM phenylmethylsulfonyl fluoride (PMSF)] for 30 s in the ice slurry. An equal amount of buffer 11 (0.1 M tris-buffered saline, pH 8.1, containing 1 mM EDTA, 1% aprotinin, 10 g/ml leupeptin, 14 µg/ml pepstatin, 4 mM PMSF, and 0.5% NP-40) was then added. The tubes were shaken for 2 hours in the The supernatant was collected for ELISA and protein measurements. The ELISA reaction was completed in 96-well plate (Dynatech, Chantilly, Va.) according to the ELISA manufacturer's instructions (GDNF $E_{max}$ ImmunoAssay Systems Kit G3520, Promega, Madison, Wis.). The optical densities were recorded in ELISA plate reader (at 450 nm wave length; Dynatech). Some lysates were diluted to ensure all the optical densities were within the standard curve. The concentrations or GDNF were calculated against six-point standard curve and then adjusted to picograms of GDNF per milligram of total protein. The total protein in each tissue lysate was measured using Bio-Rad protein assay kit (Bio-Rad, Richmond, Calif.).) for long-term gene expression. Robust GDNF immunoreactivity was seen in the right caudate, right putamen, and left ventral midbrain in both animals. In the right substantia nigra, many GDNF-immunoreactive neurons were seen. This labeling represents retrograde transport of GDNF after injections of lenti-GDNF into the right striatum. Further, dense GDNF-immunoreactive fiber staining, representing anterograde transport of the trophic factor, was seen within the right substantia nigra pars reticulate. Tissue punches taken at the time of death revealed significant levels of GDNF produced by striatal cells 8 months after lenti-GDNF injections. On the side without a striatal injection, 0.130±0.062 and 0.131±0.060 ng/mg protein of GDNF were seen in the caudate nucleus and putamen, respectively. Significantly higher GDNF levels were observed within the caudate nucleus (2.25±0.312 ng/mg protein; P<0.001) and putamen (3.5±0.582 ng/mg protein; P<0.001) on the lenti-GDNF-injected side.

This demonstrates that delivery of GDNF cDNA into the nigrostriatal system using a lentiviral vector system can potently reverse the structural and functional effects of dopamine insufficiency in nonhuman primate models of aging and early Parkinson's disease. Most importantly, lenti-GDNF delivery prevented the motor deficits that normally occur after MPTP administration. In this regard, functional disability was prevented on both a subjective clinical rating scale modeled after the Unified Parkinson's Disease Rating Scale and an objective operant motor test. Consistent expression of GDNF was observed in aged and lesioned monkeys with significant and biologically relevant levels of GDNF observed for up to 8 months after lentivirus injection. Indeed, the 2.5 to 3.5 ng/mg protein of GDNF produced after lenti-GDNF injections compares very favorably to the 50 to 152 pg/mg protein of striatal GDNF produced after intrastriatal adenovirus injections in monkeys (Kozlowski et al. 2000).

This consistent gene expression occurred without significant toxicity to aged monkeys, and minor toxicity in two of the MPTP-treated monkeys, supporting our previous observations (Kordower et al. 1999b). Pathological analyses revealed only a mild necrosis from multifocal random hepatocellular coagulation in these animals, and this was not deemed to be the cause of death of the two monkeys that died. No other young adult or aged monkeys from this study displayed morbidity or mortality after lentivirus injections. Further, detailed necropsies from the remaining MPTP-treated animals failed to reveal any relevant pathology. Although the absolute cause of death of the two monkeys remains elusive, it is submitted that the death of these two monkeys relates to the impact of the surgical procedure 1 week after the MPTP injections and is unrelated to the lentivirus injection.

In aged monkeys, lentiviral delivery of GDNF augmented host nigrostriatal function as determined by a variety of morphological, physiological, and neurochemical dependent measures. In this regard, lenti-GDNF increased the size and number of TH-immunoreactive neurons within the substantia nigra; increased the expression of TH mRNA within these neurons; increased the levels of dopamine, dopaminergic metabolites, and dopaminergic markers in the striatum; and increased FD uptake within the striatum as determined by PET scan. Enhanced nigrostriatal dopamine function was consistently associated with the expression of lentivirally delivered GDNF, as enhanced nigrostriatal function was only seen on the side with robust gene expression.

Aged monkeys were used to model specific cellular changes that occur in aging and the earliest aspects of PD. Phenotypic down-regulation of the TH gene and protein are among the earliest pathological events seen within the substantia nigra in PD (Kastner et al. 1993), and analogous changes are seen in aged rhesus monkeys (Emborg et al. 1998). The number of TH-immunoreactive nigral neurons seen in lenti-βGal-injected animals was similar to that previously reported for aged rhesus monkeys (Emborg et al. 1998). In contrast, lenti-GDNF-treated aged monkeys displayed nigral neurons in numbers similar to those seen in young adult animals. The possibility that the lenti-GDNF spurred neurogenesis of dopaminergic nigral neurons cannot be ruled out. However, the delivery of lenti-GDNF to the nigral region resulted in transgene expression throughout the midbrain. Yet, TH-immunoreactive neurons were observed only within established catecholaminergic nuclei and not in ectopic midbrain locations. A more parsimonious explanation is that GDNF up-regulated TH-immunoreactivity in aged nigral neurons that had previously down-regulated TH expression below detectable levels. The enhanced TH mRNA expression seen within nigral neurons after lenti-GDNF treatment supports this interpretation.

Lenti-GDNF also prevented the behavioral and neuroanatomical effects of MPTP-induced nigrostriatal degeneration. It is notable that, unlike many other neuroprotection paradigms, the lenti-GDNF injections were performed after the parkinsonian state was initiated, thus better modeling what can be attempted in PD patients. It is clear that neuroprotection was achieved within the substantia nigra by lenti-GDNF, as these neurons do not degenerate within a week of MPTP treatment (Kozlowski et al. 2000). However, striatal fibers can degenerate during this time, and the GDNF may be preventing degeneration or inducing sprouting of degenerating fibers. Indeed, there is evidence for both mechanisms as some animals displayed fiber morphology and topography indicative of regeneration.

It is notable that all lenti-GDNF-treated monkeys had complete preservation of nigral perikarya. Functional recovery on the hand-reach task was absent only in the one monkey with sparsest striatal reinnervation. The failure to potently protect dopaminergic innervation in the one monkey may be due to variability in the speed by which nigrostriatal fibers are lost after MPTP. At the time of the lenti-GDNF injections, dopaminergicfibers in this monkey may have regressed to a level where access to the GDNF was limited, and regrowth to the striatum was impossible.

Not only was lenti-GDNF capable of preventing the degeneration of nigrostriatal neurons in MPTP-treated monkeys, it augmented many of the morphological parameters relative to the "intact" side. It is likely that the unilateral 3-mg MPTP dose induced a small loss of TH-immunoreactive neurons on the contralateral side. Thus the increased numbers of TH-immunoreactive neurons may reflect complete neuroprotection on the side of GDNF expression contrasted with a small loss of TH-immunoreactive neurons on the side not injected.

Lentivirus was injected into both the striatum and substantia nigra in order to maximize the chance for an effect. In practice, the skilled artisan will, without undue experimentation determine the regions of GDNF delivery to maximize reversal of progressive nigrostriatal degeneration, e.g., from teachings in the art and this disclosure, considering such factors as the importance of related biological events such as anterograde transport of GDNF from injection sites to target regions. And, the skilled artisan, without undue experimentation, from this disclosure and the knowledge in the art can evaluate potential adverse events resulting from lenti-GDNF inducing supranormal levels of striatal dopamine; and, vectors with built-in inducible systems that can modulate gene expression in cases of dose-limiting side effects may be useful.

The reversal of slowly progressive cellular phenotypic changes seen in aged monkeys, combined with the structural and functional neuroprotection and regeneration seen in MPTP-treated monkeys, as shown herein, indicates that lentiviral delivery of GDNF can provide potent clinical benefits for patients with neurodegenerative diseases, conditions, maladies and the like, such as PD.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCE LIST

C. Honey, R. E. Gross, A. M. Lozano, *Can. J. Neurol. Sci.* 2, S45 (1999).
A. Björklund, C. Rosenblad, C. Winkler, D. Kirik, *Neurobiol. Dis.* 4,196 (1997).
J. L. Tseng, E. E. Baetge, A. D. Zurn, P. Aebischer, *J. Neurosci.* 17, 325 (1997).
P. A. Lapchak, D. M. Gash, S. Jiao, P. J. Miller, D. Hilt, *Exp. Neurol.* 144, 29 (1997).
D. M. Gash, G. A. Gerhardt, B. J. Hoffer, *Adv. Pharmacol.* 42, 11 (1998).
C. M. Kearns and D. M. Gash, *Brain Res.* 672, 104 (1995).
D. L. Choi-Lundberg, et al., *Science* 275, 838 (1997).
D. M. Gash et al., *Nature* 380 252 (1996).
J. H. Kordower, et al., *Ann. Neurol.* 46, 419 (1999a).
L. Naldini, et al., *Science* 272, 263 (1996).
M. Takahashi, H. Miyoshi, I. M. Verma, F. H. Gage, *J. ViroL.* 73, 7812 (1999).
K. A. Mitrophanous, et al., *Gene Ther.* 6, 1808 (1999).
G. Wang, et al., *J. Clin. Invest* 104, 55 (1999).
N. Déglon et al., *Hum. Gene Ther.* 11, 179, (2000).
J. H. Kordower, et al., *Exp. Neurol.* 160,1 (1999b).
M. E. Emborg, et al., *J. Comp. Neurol.* 401, 253 (1998).
A. Kastner, E. C. Hirsh, Y. Agid, F. Javoy Agid, *Brain Res.* 606, 341 (1993).
J. H. Kordower, *Cell Transplant* 4, 155 (1995).
D. A. Kozlowski et al., *ASNTR*, Abstr. 7, 25 (2000).
J. L. Eberling, et al., *Brain Res.* 832, 184 (1999).
B. Connor, et al., *Gene Ther.* 6, 1936 (1999).
C. Rosenblad, D. Kirik, A. Björklund, *Exp. Neurol.* 16, 503 (2000).

C. Rosenblad et al., *Mol Cell Neurosci.* 15(2), 199–214 (2000).
J. E. Springer et al., *Exp Neurol.* 127(2), 167–70 (1994).
C. E. Henderson et al., *Science.* 266(5187), 1062–4 (1994); see also *Science.* 266(5187), 970–2 (1994); *Science.* 267 (5199), 777 (1995).
C. Suter-Crazzolara et al., *Neuroreport.* 5(18), 2486–8 (1994).
M. D. Lindner et al., *Exp Neurol.* 132(1), 62–76 (1995).
D. Schindelhauer et al., *Genomics.* 28(3), 605–7 (1995).
N. Bermingham et al., *Hum Genet.* 96(6), 671–3 (1995).
N. Matsushita et al., *Gene.* 203(2), 149–57 (1997).
D. Woodbury et al., *Brain Res.* 803(1–2), 95–104 (1998).
L. Grimm et al., *Hum Mol Genet.* 7(12), 1873–86 (1998).
P. A. Baecker et al., *Brain Res Mol Brain Res.* 69(2), 209–22 (1999).
Kaplitt et al., U.S. Pat. No. 6,180,613.
R. Zufferey et al., *Journal of Virology.* 77(12), 9873–9880 (1998).

What is claimed is:

1. A method for treating Parkinson's disease in a mammal in need of such treatment comprising administering a lentiviral vector to a target cell in the brain of the mammal, said lentiviral vector comprising a nucleic acid sequence comprising a sequence encoding human glial cell line derived neutrotrophic factor (GDNF) operably linked to a promoter, wherein GDNF is expressed in the target cell thereby treating said Parkinson's disease, such that nigrostriatal degeneration is reduced.

2. The method of claim 1, wherein the lentiviral vector is an EIAV.

3. The method of claim 1, wherein the lentiviral vector is an HIV.

4. The method of claim 1, wherein the lentiviral vector is an SIV.

5. The method of claim 1, wherein the lentiviral vector is an FIV.

6. The method of claim 1, wherein the lentiviral vector is a nonprimate lentiviral vector.

7. The method of claim 1, wherein the mammal is a primate.

8. The method of claim 7 wherein the primate is a human.

9. The method of claim 1, wherein the administering is intracranially.

10. The method of claim 1, wherein the administering is by retrograde transport.

11. The method of claim 1, wherein there is GDNF expression for a duration of up to 8 months.

12. The method of claim 1, wherein motor deficits due to said Parkinson's disease are reversed.

13. The method of claim 1, wherein the method induces nigrostriatal regeneration.

14. The method of claim 9 wherein the administering intracranially is to the striatum.

15. The method of claim 9 wherein the administering intracranially is to the substantia nigra.

* * * * *